(12) United States Patent
Aoki et al.

(10) Patent No.: US 10,605,765 B2
(45) Date of Patent: Mar. 31, 2020

(54) GAS DETECTION DEVICE

(71) Applicant: Toyota Jidosha Kabushiki Kaisha, Toyota-shi, Aichi-ken (JP)

(72) Inventors: Keiichiro Aoki, Shizuoka-ken (JP); Kazuhiro Wakao, Susono (JP); Kazuhisa Matsuda, Susono (JP)

(73) Assignee: Toyota Jidosha Kabushiki Kaisha, Toyota-shi, Aichi-ken (JP)

( * ) Notice: Subject to any disclaimer, the term of this patent is extended or adjusted under 35 U.S.C. 154(b) by 140 days.

(21) Appl. No.: 15/841,924

(22) Filed: Dec. 14, 2017

(65) Prior Publication Data
US 2018/0172624 A1   Jun. 21, 2018

(30) Foreign Application Priority Data
Dec. 19, 2016   (JP) .................. 2016-245515

(51) Int. Cl.
G01N 27/407   (2006.01)
G01N 33/00    (2006.01)

(52) U.S. Cl.
CPC ....... G01N 27/4074 (2013.01); G01N 27/407 (2013.01); G01N 33/0042 (2013.01); Y02A 50/248 (2018.01)

(58) Field of Classification Search
CPC ............. G01N 27/407; G01N 27/4074; G01N 33/0042
See application file for complete search history.

(56) References Cited

U.S. PATENT DOCUMENTS

| | | | |
|---|---|---|---|
| 6,083,370 A | 7/2000 | Kato et al. | |
| 2002/0043460 A1 | 4/2002 | Ikeda | |
| 2016/0146085 A1* | 5/2016 | Mizutani | F01N 11/00 60/274 |

FOREIGN PATENT DOCUMENTS

| | | |
|---|---|---|
| CN | 105393115 A | 3/2016 |
| JP | H10232220 A | 9/1998 |
| JP | 2002071633 A | 3/2002 |
| JP | 2009053108 A | 3/2009 |
| JP | 2015017931 A | 1/2015 |
| WO | 2015004846 A1 | 1/2015 |

OTHER PUBLICATIONS

U.S. Appl. No. 15/796,219, filed Oct. 27, 2017; Inventors: Keiichiro Aoki et al.

* cited by examiner

Primary Examiner — Luan V Van
Assistant Examiner — Caitlyn Mingyun Sun
(74) Attorney, Agent, or Firm — Dinsmore & Shohl LLP

(57) ABSTRACT

A gas detection device includes a voltage applying unit configured to apply a voltage across a first electrode and a second electrode of an electrochemical cell and a measurement control unit configured to perform a first application voltage sweep and a second application voltage sweep which have different sweeping voltage ranges, to acquire a first parameter based on the output current of the first application voltage sweep, to acquire a second parameter based on the output current of the second application voltage sweep, to calculate a SOx detection parameter which is a difference or a ratio between the first parameter and the second parameter, and to perform determination of whether sulfur oxides with a predetermined concentration or higher are contained in an exhaust gas or detection of a concentration of sulfur oxides in the exhaust gas based on the SOx detection parameter.

7 Claims, 16 Drawing Sheets

GAS DETECTION DEVICE

CROSS-REFERENCE TO RELATED APPLICATIONS

This application claims priority to Japanese Patent Application No. 2016-245515 filed on Dec. 19, 2016, which is incorporated herein by reference in its entirety.

BACKGROUND

1. Technical Field

The disclosure relates to a gas detection device that can determine whether sulfur oxides with a predetermined concentration or more are contained in an exhaust gas (a sample gas) of an internal combustion engine or detect the concentration of sulfur oxides contained in the exhaust gas.

2. Description of Related Art

An air-fuel ratio sensor (hereinafter also referred to as an "A/F sensor") that acquires an air-fuel ratio (A/F) of an air-fuel mixture in a combustion chamber based on a concentration of oxygen ($O_2$) contained in an exhaust gas has been widely used to control an internal combustion engine. A limiting current type gas sensor is known as such a type of air-fuel ratio sensor.

A SOx concentration detection device (hereinafter also referred to as a "conventional device") that detects a concentration of sulfur oxides (hereinafter also referred to as "SOx") in an exhaust gas using such a limiting current type gas sensor has been proposed (for example, see Japanese Unexamined Patent Application Publication No. 2015-17931 (JP 2015-17931 A)).

The conventional device includes a sensing cell (an electrochemical cell) using an oxygen pumping effect of a solid electrolyte with oxygen ion conductivity. The conventional device generates oxide ions ($O^{2-}$) by applying a voltage across a pair of electrodes of the sensing cell to decompose gas components containing an oxygen atom (such as $O_2$, SOx, and $H_2O$ which are also referred to as "oxygen-containing components") in an exhaust gas. The conventional device detects characteristics of a current flowing between the electrodes of the sensing cell due to migration of oxide ions, which have been generated by decomposition of the oxygen-containing components, between the electrodes (an oxygen pumping effect).

Specifically, when a SOx concentration is detected, the conventional device performs an application voltage sweep. That is, the conventional device performs an application voltage sweep of stepping up an application voltage applied to the sensing cell from 0.4 V to 0.8 V and then stepping down the application voltage from 0.8 V to 0.4 V.

The conventional device calculates the SOx concentration using a difference between a reference current which is a "current (hereinafter referred to as an "electrode current" or an "output current") flowing between the electrodes of the sensing cell at a time point at which the application voltage reaches 0.8 V and a "peak value" which is a minimum value of the output current in a period in which the application voltage is stepped down from 0.8 V to 0.4 V.

SUMMARY

However, there is a high likelihood that the output current will change due to an influence of oxygen-containing components other than SOx contained in the exhaust gas. For example, a decomposition voltage of water ($H_2O$) is substantially equal to a decomposition voltage of sulfur oxides or slightly higher than the decomposition voltage of sulfur oxides. A water concentration in the exhaust gas changes, for example, depending on an air-fuel ratio of an air-fuel mixture. Accordingly, it is difficult to detect an output current resulting from only decomposition of SOx components with an influence from decomposition of water on the output current removed. Accordingly, there is demand for accurately performing determination of whether sulfur oxides with a predetermined concentration or higher are contained in an exhaust gas or detection of the concentration of sulfur oxides in the exhaust gas using an "output current change due to only SOx components without being affected by oxygen-containing components other than SOx."

In a plurality of gas sensors of the same type, output current characteristics when an application voltage sweep for detecting an SOx concentration is performed vary between the individual gas sensors due to differences in capacitive component and resistive component of a solid electrolyte and electrodes between the gas sensors which are caused by individual differences between the gas sensors or differences in aging between the gas sensors. Accordingly, when the application voltage sweep is performed, a value of a parameter for detecting a SOx concentration, which varies depending on the SOx concentration in the exhaust gas, varies depending on the individual differences between the gas sensors or the differences in aging between the gas sensors and thus detection accuracy of the SOx concentration deteriorates. Accordingly, there is more demand for more accurately performing determination of whether sulfur oxides with a predetermined concentration or higher are contained in an exhaust gas or detection of the concentration of sulfur oxides in an exhaust gas using an "output current change with a reduced variation due to an individual difference between gas sensors or a difference in aging between gas sensors."

The disclosure provides a gas detection device (hereinafter also referred to as an "invented detection device") that can accurately perform determination of whether sulfur oxides with a predetermined concentration or higher are contained in an exhaust gas or detection of the concentration of sulfur oxides.

A gas detection device according to an aspect of the disclosure includes: an element portion which is disposed in an exhaust gas passage of an internal combustion engine, which includes an electrochemical cell including a solid electrolyte with oxide ion conductivity and a first electrode and a second electrode which are formed on surfaces of the solid electrolyte, and a diffusion resistor formed of a porous material being able to transmit an exhaust gas flowing in the exhaust gas passage, and in which the exhaust gas flowing in the exhaust gas passage reaches the first electrode via the diffusion resistor; a voltage applying unit configured to apply a voltage across the first electrode and the second electrode; a current detecting unit configured to detect an output current which is a current flowing between the first electrode and the second electrode; and a measurement control unit configured to control an application voltage which is a voltage applied across the first electrode and the second electrode using the voltage applying unit, to acquire the output current using the current detecting unit, and to perform determination of whether sulfur oxides with a predetermined concentration or higher are contained in the exhaust gas or detection of a concentration of sulfur oxides in the exhaust gas based on the acquired output current. The measurement control unit is configured to perform a first application voltage sweep of performing a first step-up sweep of stepping up the application voltage from a first voltage which is selected in a first voltage range higher than a lower limit voltage of a limiting current region in which the output current is a limiting current of oxygen and lower than a decomposition start voltage of sulfur oxides to a second voltage which is higher than the first voltage and equal to or lower than a voltage higher by a predetermined value than the decomposition start voltage of sulfur oxides and then performing a first step-down sweep of stepping down the application voltage from the second voltage to the first voltage in at least one cycle and to acquire a first parameter using at least the output current in the first step-down sweep and using a predetermined first specific method. The measurement control unit is configured to perform a second application voltage sweep of performing a second step-up sweep of stepping up the application voltage from a third voltage which is selected in the first voltage range to a fourth voltage which is higher than the decomposition start voltage of sulfur oxides and higher than the second voltage and then performing a second step-down sweep of stepping down the application voltage from the fourth voltage to the third voltage using the voltage applying unit in at least one cycle after the first application voltage sweep is performed and to acquire a second parameter having a correlation with a degree of change occurring in the output current, which increases as the concentration of sulfur oxides contained in the exhaust gas increases, due to a current flowing between the first electrode and the second electrode due to return of sulfur adsorbed on the first electrode to sulfur oxides by a reoxidation reaction in the first electrode when the application voltage is lower than the decomposition start voltage of sulfur oxides in a period in which the second step-down sweep is performed using at least the output current in the second step-down sweep and using the same second specific method as the first specific method. The measurement control unit is configured to calculate a difference or a ratio between the first parameter and the second parameter as a SOx detection parameter and to perform determination of whether sulfur oxides with a predetermined concentration or higher are contained in the exhaust gas or detection of the concentration of sulfur oxides in the exhaust gas based on the SOx detection parameter.

According to the inventor's research, it was proved that an "output current change" which is not easily affected by "oxygen-containing components other than sulfur oxides" due to return of "sulfur adsorbed on the first electrode when a step-down sweep is performed" to sulfur oxides by reoxidation in the first electrode occurs. It was also proved that a degree of "output current change" changes greatly depending on a voltage drop per predetermined elapsed time (that is, a step-down rate) in the step-down sweep (see FIGS. 4A and 4B). A mechanism by which such a phenomenon occurs is thought to be as follows.

That is, sulfurs (a decomposition product of sulfur oxides) adsorbed on the first electrode by performing a step-up sweep is returned to sulfur oxides by reoxidation in the first electrode when a step-down sweep is performed. Decomposition products (for example, hydrogen which is a decomposition product of water) of oxygen-containing components other than sulfur oxides are not adsorbed on the first electrode when the step-up sweep is performed. Accordingly, the phenomenon that a decomposition product of oxygen-containing components other than sulfur oxides is returned to the oxygen-containing components by reoxidation in the first electrode does not occur substantially when the step-down sweep is performed.

Accordingly, the "output current change" which is caused due to return of sulfurs adsorbed on the first electrode to sulfur oxides by reoxidation in the first electrode when the step-down sweep is performed is not easily affected by oxygen-containing components other than sulfur oxides. That is, an "output current change" which is not easily affected by oxygen-containing components other than sulfur oxides occurs during the step-down sweep.

When a step-down rate (a sweeping rate) of the step-down sweep is lower than a certain rate, a reoxidation reaction of sulfur progresses continuously and slowly in the step-down sweep. Accordingly, hardly any degree of "output current change" appears even irrespective of the value of the sulfur oxides concentration.

On the other hand, when the step-down rate of the step-down sweep is higher than a certain rate, the application voltage decreases without such progress of the reoxidation reaction of sulfur in the step-down sweep. When the application voltage becomes a voltage in a certain voltage "range in which the reoxidation reaction of sulfur is activated (that is, a predetermined voltage range which is less than a decomposition start voltage of sulfur oxides)," the degree of output current change increases as the sulfur oxides concentration increases due to a rapid process of the reoxidation reaction of sulfur (an increase of a reoxidation reaction rate of sulfur, that is, a rapid increase of an occurrence frequency of the reoxidation reaction of sulfur). That is, a significant current change occurs in accurate detection of the sulfur oxides concentration.

Therefore, the step-down rate of the step-down sweep is set to a "rate at which the reoxidation reaction rate of sulfur increases rapidly from a time point at which the application voltage becomes a voltage in the predetermined voltage range less than the decomposition start voltage of sulfur oxides." Accordingly, an output current change which is not affected by oxygen-containing components other than sulfur oxides appears to be greater as the sulfur oxides concentration becomes higher.

The gas detection device according to this aspect acquires the second parameter as a parameter having a correlation with a "degree of change of the output current" due to the reoxidation reaction of sulfur. Accordingly, the second parameter is a parameter which changes depending on the concentration of sulfur oxides in the exhaust gas.

In results of repeated study of the inventor of the disclosure, it was proved that an output current characteristics vary due to individual differences between even gas sensors (element portions) of the same type and thus the magnitude of the second parameter varies. That is, the second parameter has a value which varies depending on the concentration of sulfur oxides in the exhaust gas and in which an influence of the individual differences between gas sensors is reflected.

On the other hand, the gas detection device according to this aspect calculates a difference or a ratio between the second parameter and the first parameter as the SOx detection parameter. The gas detection device performs determination of whether sulfur oxides with a predetermined concentration or higher are contained in the exhaust gas or detection of the concentration of sulfur oxides in the exhaust gas based on the calculated SOx detection parameter. The SOx detection parameter is a parameter depending on the concentration of sulfur oxides in the exhaust gas and is also a parameter in which an influence of components varying due to the individual differences between the gas sensors is reduced. Accordingly, the first detection device can accurately perform determination of whether sulfur oxides with a predetermined concentration or higher are contained in the exhaust gas or detection of the concentration of sulfur oxides in the exhaust gas.

In the aspect, a step-down rate of the second step-down sweep may be set to a rate at which a rate of the reoxidation reaction increases rapidly at a time point at which the application voltage reaches a voltage in a voltage range which is within the first voltage range and higher than the third voltage, and the first application voltage sweep and the second application voltage sweep may have the same sweeping rate which is expressed by a voltage change per unit time.

According to this configuration, an influence from individual differences between the gas sensors on the first parameter is equal to or closer to an influence from the individual differences between the gas sensors on the second parameter. Accordingly, the SOx detection parameter which is a difference or a ratio between the first parameter and the second parameter is a parameter from which an influence of components varying due to the individual differences between the gas sensors are more accurately removed. Accordingly, the first detection device can more accurately perform determination of whether sulfur oxides with a predetermined concentration or higher are contained in the exhaust gas or detection of the concentration of sulfur oxides in the exhaust gas.

In the aspect, the measurement control unit may be configured to use a method of setting the application voltage to an air-fuel ratio detection application voltage in the limiting current region using the voltage applying unit before the first application voltage sweep is performed, acquiring the output current detected by the current detecting unit as the first current when the application voltage is set to the air-fuel ratio detection application voltage, acquiring a value having a specific correlation with the output current in a predetermined first period in the first step-down sweep as a second current based on the output current detected by the current detecting unit, and calculating a difference between the acquired first current and the acquired second current as the first specific method to acquire the calculated difference as the first parameter, and the measurement control unit may be configured to use a method of setting the application voltage to the air-fuel ratio detection application voltage using the voltage applying unit after the first application voltage sweep is performed and before the second application voltage sweep is performed, acquiring the output current detected by the current detecting unit when the application voltage is set to the air-fuel ratio detection application voltage as a third current, acquiring a value having a specific correlation with the output current in a second period in which the application voltage is in a range which is higher than the third voltage and equal to or lower than the decomposition start voltage of sulfur oxides in the second step-down sweep as a fourth current based on the output current detected by the current detecting unit, and calculating a difference between the acquired third current and the acquired fourth current as the second specific method to acquire the calculated difference as the second parameter.

According to this configuration, the difference calculated using the method of calculating the difference between the first current and the second current is acquired as the first parameter. The second current does not depend on the concentration of sulfur oxides in the exhaust gas but changes due to an influence of a concentration of oxygen in the exhaust gas. On the other hand, an influence of the concentration of oxygen in the exhaust gas on the second current appears in the first current. Accordingly, the first parameter which is a difference between the first current and the second current is not or hardly affected by any of the influence of the concentration of oxygen in the exhaust gas and the influence of the concentration of sulfur oxides in the exhaust gas and has a value in which the influence of the individual differences between the gas sensors is reflected.

According to this configuration, the difference calculated using the method of calculating the difference between the third current and the fourth current is acquired as the second parameter. The fourth current changes due to influences of a concentration of sulfur oxides in the exhaust gas and a concentration of oxygen in the exhaust gas. On the other hand, an influence of the concentration of oxygen in the exhaust gas on the fourth current appears in the third current. Accordingly, the second parameter which is a difference between the third current and the fourth current is not or hardly affected by the influence of the concentration of oxygen in the exhaust gas and has a value which varies depending on the concentration of sulfur oxides and in which the influence of the individual differences between the gas sensors is reflected.

According to this configuration, the difference or the ratio between the first parameter and the second parameter which have been acquired as described above is calculated as the SOx detection parameter. Then, determination of whether sulfur oxides with a predetermined concentration or higher are contained in the exhaust gas or detection of the concentration of sulfur oxides in the exhaust gas is performed based on the calculated SOx detection parameter. The SOx detection parameter is a parameter based on the concentration of sulfur oxides in the exhaust gas and has a value in which an influence of components varying due to the individual differences between the gas sensors is reduced from the second parameter and in which an influence of the concentration of oxygen is also removed.

According to this configuration, determination of whether sulfur oxides with a predetermined concentration or higher are contained in the exhaust gas or detection of the concentration of sulfur oxides in the exhaust gas is performed using the SOx detection parameter. Accordingly, the invented detection device can accurately perform determination of whether sulfur oxides with a predetermined concentration or higher are contained in the exhaust gas or detection of the concentration of sulfur oxides in the exhaust gas.

In the aspect, the measurement control unit may be configured to acquire the output current detected by the current detecting unit when the application voltage is a predetermined current detection voltage in a range which is higher than the first voltage and equal to or lower than the decomposition start voltage of sulfur oxides in the first step-down sweep as the second current which has a value having the specific correlation with the output current in the first period, and the measurement control unit may be configured to acquire the output current detected by the current detecting unit when the application voltage is the current detection voltage in the second step-down sweep as the fourth current which has a value having the specific correlation with the output current in the second period.

According to this configuration, the output current at a time point at which the application voltage which has been proved to change depending on the concentration of sulfur oxides by an experiment (see FIGS. 7A, 7B, and 7C) becomes a "current acquisition voltage" in the second step-down sweep is acquired as the fourth current, and the output current at a time point at which the application voltage becomes the current acquisition voltage in the first step-down sweep is acquired as the second current. Accordingly, the second parameter which is a difference between the second current and the fourth current is a parameter which accurately indicates the concentration of sulfur oxides.

According to this configuration, it is possible to accurately perform determination of whether sulfur oxides with a predetermined concentration or higher are contained in the exhaust gas or detection of the concentration of sulfur oxides in the exhaust gas based on the SOx detection parameter which is a difference or a ratio between the second parameter and the first parameter.

In the aspect, the measurement control unit may be configured to determine whether a magnitude of a difference between the first current and the third current is equal to or less than a threshold difference value, and the measurement control unit may be configured to perform the determination of whether sulfur oxides with a predetermined concentration or higher are contained in the exhaust gas or the detection of the concentration of sulfur oxides in the exhaust gas only when the magnitude of the difference is equal to or less than the threshold difference value.

When the magnitude (the absolute value) of the difference between the first current and the third current is excessively large, a likelihood that the SOx detection parameter will accurately indicate only the output current change due to a reaction of SOx decreases due to the influence thereof. Accordingly, in this configuration, determination of whether sulfur oxides with a predetermined concentration or higher are contained in the exhaust gas or detection of the concentration of sulfur oxides in the exhaust gas is performed only when the magnitude of the difference between the first current and the third current is small. By employing this configuration, it is possible to accurately perform determination of whether sulfur oxides with a predetermined concentration or higher are contained in the exhaust gas or detection of the concentration of sulfur oxides in the exhaust gas.

In the aspect, the measurement control unit may be configured to detect the concentration of sulfur oxides based on the SOx detection parameter and the third current.

According to this configuration, the concentration of sulfur oxides in the exhaust gas is detected based on the SOx detection parameter accurately indicating the concentration of sulfur oxides in the exhaust gas and the third current. In this case, when the third current changes, the value of the SOx detection parameter also changes. The concentration of sulfur oxides is detected in consideration of the change. Accordingly, it is possible to accurately detect the concentration of sulfur oxides in the exhaust gas.

In the aspect, the measurement control unit may be configured to determine whether a magnitude of the SOx detection parameter is equal to or greater than a predetermined threshold value, and the measurement control unit may be configured to determine that sulfur oxides with a predetermined concentration or higher are contained in the exhaust gas when it is determined that the magnitude of the SOx detection parameter is equal to or greater than the threshold value, and to determine that sulfur oxides with a predetermined concentration or higher are not contained in the exhaust gas when it is determined that the magnitude of the SOx detection parameter is less than the threshold value.

According to this configuration, it is possible to accurately perform determination of whether sulfur oxides with a predetermined concentration or higher are contained in the exhaust gas by determining whether the magnitude of the SOx detection parameter accurately indicating the concentration of sulfur oxides is equal to or greater than a "predetermined threshold value corresponding to a predetermined concentration."

In the above description, for the purpose of easy understanding of the disclosure, names which are used in an embodiment which will be described later are added in parentheses to elements of the disclosure corresponding to the embodiment. However, the elements of the disclosure are not limited to the embodiment defined by the names. Other objects, features, and advantages of the disclosure will be easily understood from the following description of the embodiment of the disclosure which will be described below with reference to the accompanying drawings.

BRIEF DESCRIPTION OF THE DRAWINGS

Features, advantages, and technical and industrial significance of exemplary embodiments of the disclosure will be described below with reference to the accompanying drawings, in which like numerals denote like elements, and wherein.

DETAILED DESCRIPTION OF EMBODIMENTS

Figure 1:
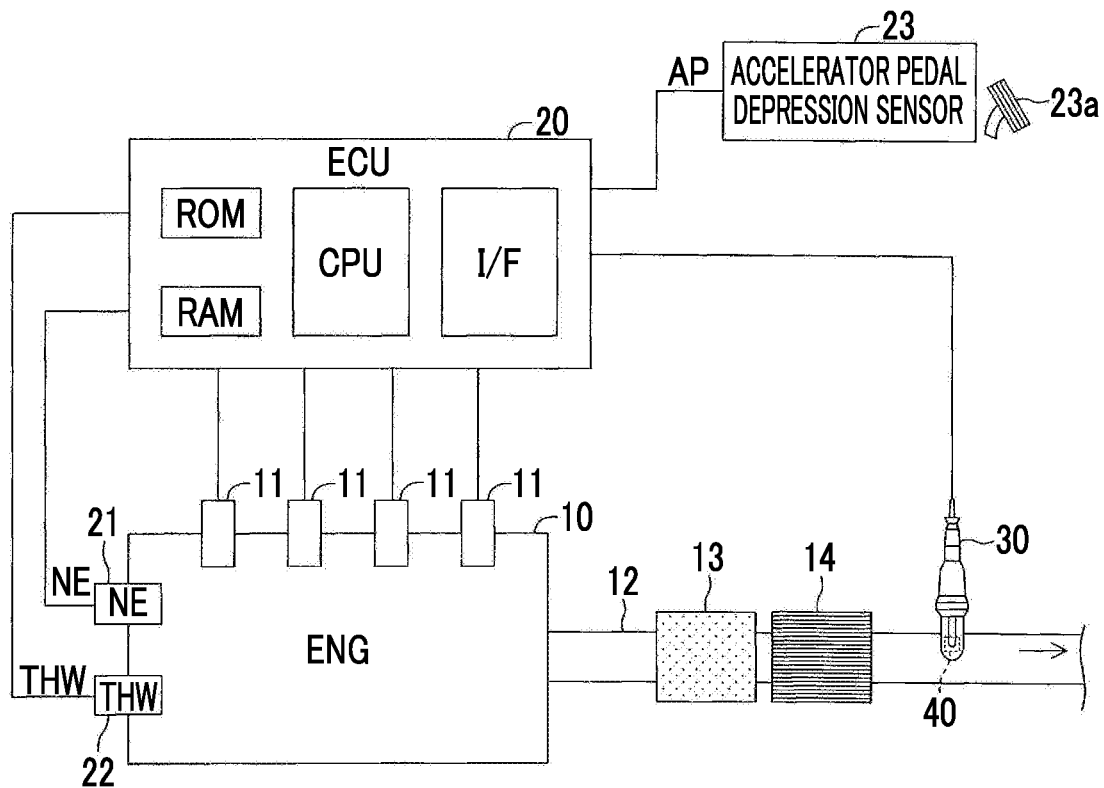
FIG. 1 is a diagram schematically illustrating a configuration of a gas detection device according to a first embodiment of the disclosure and an internal combustion engine to which the gas detection device is applied.

Hereinafter, gas detection devices according to embodiments of the disclosure will be described with reference to the accompanying drawings. In the drawings of the embodiments, the same or corresponding elements will be referenced by the same reference signs.

First Embodiment

A gas detection device according to a first embodiment of the disclosure (hereinafter also referred to as a "first detection device") will be described below. The first detection device is applied to an "internal combustion engine 10 illustrated in FIG. 1" mounted in a vehicle which is not illustrated.

The internal combustion engine 10 is a well-known diesel engine. The internal combustion engine 10 includes a combustion chamber which is not illustrated and a fuel injection valve 11. The fuel injection valve 11 is disposed in a cylinder head portion and injects fuel into the combustion chamber. The fuel injection valve 11 directly injects fuel into the combustion chamber in accordance with an instruction from an ECU 20 which will be described later. An exhaust pipe 12 is connected to an end of an exhaust gas manifold which is not illustrated and is connected to an exhaust port communicating with the combustion chamber which is not illustrated. The exhaust port, the exhaust gas manifold, and the exhaust pipe 12 constitute an exhaust gas passage in which exhaust gas discharged from the combustion chamber flows. A diesel oxidation catalyst (DOC) 13 and a diesel particulate filter (DPF) 14 are disposed in the exhaust pipe 12.

The DOC 13 is an exhaust gas purification catalyst. Specifically, the DOC 13 oxidizes unburned components (HC and CO) in the exhaust gas to purify the exhaust gas using precious metals such as platinum and palladium as a catalyst. That is, by the DOC 13, HC is oxidized to water and $CO_2$, and CO is oxidized to $CO_2$.

The DPF 14 is disposed downstream from the DOC 13. The DPF 14 is a filter that captures particulates in the exhaust gas. Specifically, the DPF 14 includes a plurality of pores formed by a porous material (for example, a diaphragm formed of cordierite which is a kind of ceramic). The DPF 14 captures particulates contained in the exhaust gas passing through the diaphragm on pore surfaces of the diaphragm.

The first detection device includes an electronic control unit (ECU) 20. The ECU 20 is an electronic control circuit including a microcomputer including a CPU, a ROM, a RAM, a backup RAM, and an interface (I/F) as a main constituent component. The CPU implements predetermined functions by executing instructions (routines) stored in the memory (ROM).

The ECU 20 is connected to various actuators of the internal combustion engine 10 (such as the fuel injection valve 11). The ECU 20 sends out a drive (instruction) signal to the actuators to control the internal combustion engine 10. The ECU 20 is connected to various sensors described below and receives signals from the sensors.

Engine Rotation Speed Sensor 21

An engine rotation speed sensor (hereinafter referred to as an "NE sensor") 21 measures a rotation speed (an engine rotation speed) NE of the internal combustion engine 10 and outputs a signal indicating the engine rotation speed NE.

Coolant Temperature Sensor 22

A coolant temperature sensor 22 is disposed in a cylinder block. The coolant temperature sensor 22 detects a temperature of a coolant (a coolant temperature THW) for cooling the internal combustion engine 10 and outputs a signal indicating the coolant temperature THW.

Accelerator Pedal Depression Sensor 23

An accelerator pedal depression sensor 23 detects an amount of operation of an accelerator pedal 23a (an accelerator depression amount) of the vehicle and outputs a signal indicating an accelerator pedal depression amount AP.

Gas Sensor 30

A gas sensor 30 is a one-cell limiting current type gas sensor and is disposed in an exhaust pipe 12 constituting an exhaust gas passage of the internal combustion engine 10. The gas sensor 30 is disposed downstream from the DOC 13 and the DPF 14 in the exhaust pipe 12.

Configuration of Gas Sensor

Figure 2:
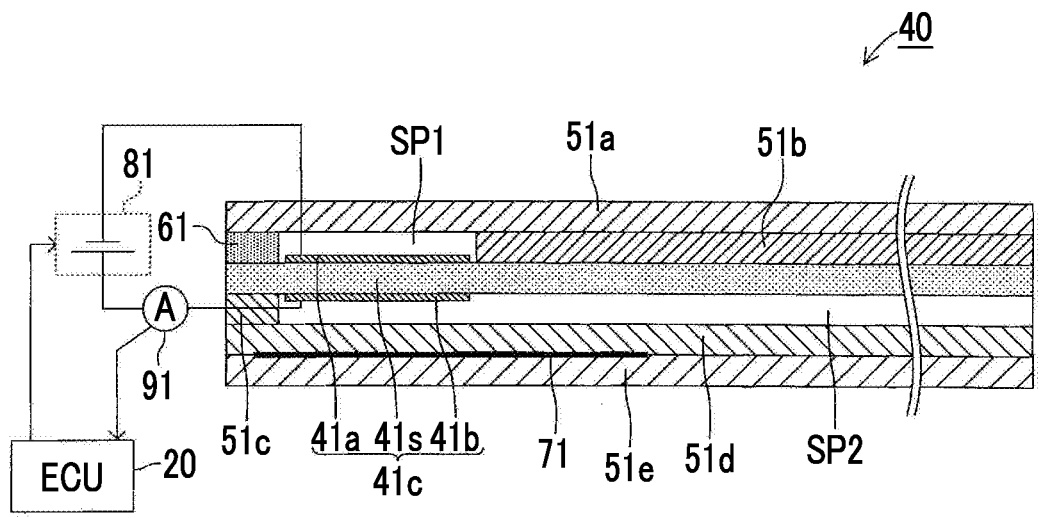
FIG. 2 is a cross-sectional view schematically illustrating an example of a configuration of an element portion of a gas sensor illustrated in FIG. 1.

A configuration of the gas sensor 30 will be described below with reference to FIG. 2. An element portion 40 included in the gas sensor 30 includes a solid electrolyte 41s, a first alumina layer 51a, a second alumina layer 51b, a third alumina layer 51c, a fourth alumina layer 51d, a fifth alumina layer 51e, a diffusion resistor portion (a diffusion rate control layer) 61, and a heater 71.

The solid electrolyte 41s is a thin plate member with oxide ion conductivity which contains zirconia. Zirconia forming the solid electrolyte 41s may contain an element such as scandium (Sc) and yttrium (Y).

Each of the first alumina layer 51a to the fifth alumina layer 51e is a dense (gas-non-transmitting) layer (a dense thin plate member) containing alumina.

The diffusion resistor portion 61 is a porous diffusion rate control layer and is a gas-transmitting layer (a thin plate member). The heater 71 is, for example, a thin plate member of cermet containing platinum (Pt) and ceramic (such as alumina) and is a heat emitter that emits heat with supply of electric power. The heater 71 is connected to a power source which is not illustrated and mounted in a vehicle via a lead wire which is not illustrated. An amount of heat emitted from the heater 71 can be changed by causing the ECU 20 to control an "amount of power supplied from the power source."

The layers of the element portion 40 are stacked from the bottom in the order of the fifth alumina layer 51e, the fourth alumina layer 51d, the third alumina layer 51c, the solid electrolyte 41s, the diffusion resistor portion 61, the second alumina layer 51b, and the first alumina layer 51a.

An internal space SP1 is formed by the first alumina layer 51a, the solid electrolyte 41s, the diffusion resistor portion 61, and the second alumina layer 51b. An exhaust gas of the internal combustion engine 10 as a sample gas is introduced into the internal space SP1 via the diffusion resistor portion 61. That is, the internal space SP1 communicates with the inside of the exhaust pipe 12 of the internal combustion engine 10 via the diffusion resistor portion 61. Accordingly, an exhaust gas in the exhaust pipe 12 is introduced as a sample gas into the internal space SP1. A first air introduction passage SP2 is formed by the solid electrolyte 41s, the third alumina layer 51c, and the fourth alumina layer 51d and is open to the atmosphere outside the exhaust pipe 12.

The first electrode 41a is fixed to one surface of the solid electrolyte 41s (specifically, the surface of the solid electrolyte 41s defining the internal space SP1). The first electrode 41a is a negative electrode. The first electrode 41a is a porous cermet electrode containing platinum (Pt) as a main component.

The second electrode 41b is fixed to the other surface of the solid electrolyte 41s (specifically, the surface of the solid electrolyte 41s defining the first air introduction passage SP2). The second electrode 41b is a positive electrode. The second electrode 41b is a porous cermet electrode containing platinum (Pt) as a main component.

The first electrode 41a and the second electrode 41b are disposed to face each other with the solid electrolyte 41s interposed therebetween. That is, the first electrode 41a, the second electrode 41b, and the solid electrolyte 41s constitute an electrochemical cell 41c having an oxygen discharge capability based on an oxygen pumping effect. The electrochemical cell 41c is heated to an activation temperature by the heater 71.

The layers including the solid electrolyte 41s and the first to fifth alumina layers 51a to 51e are formed in a sheet shape, for example, using a doctor blade method or an extrusion molding method. The first electrode 41a, the second electrode 41b, wires for supplying power to the electrodes, and the like are formed, for example, using a screen printing method. By stacking and baking such sheets as described above, the element portion 40 having the above-mentioned structure is integrally formed.

A material of the first electrode 41a is not limited to the above-mentioned materials and can be selected, for example, from materials containing a platinum group element such as platinum (Pt), rhodium (Rh), or palladium (Pd) or an alloy thereof as a main component. The material of the first electrode 41a is not particularly limited as long as SOx contained in a sample gas introduced into the internal space SP1 via the diffusion resistor portion 61 can be reductively decomposed when a voltage equal to or higher than a decomposition start voltage (specifically, a voltage of about 0.6 V or more) of SOx is applied between the first electrode 41a and the second electrode 41b.

The gas sensor 30 includes a power supply circuit 81 and an ammeter 91. The power supply circuit 81 and the ammeter 91 are connected to the ECU 20.

The power supply circuit 81 is configured to apply a predetermined voltage (hereinafter also referred to as an "application voltage Vm") across the first electrode 41a and the second electrode 41b such that the potential of the second electrode 41b is higher than the potential of the first electrode 41a. The power supply circuit 81 can change the application voltage Vm under the control of the ECU 20.

The ammeter 91 measures an output current (an electrode current) Im which is a current flowing between the first electrode 41a and the second electrode 41b (that is, a current flowing in the solid electrolyte 41s) and outputs the measured value to the ECU 20.

Outline of Operation

An outline of the operation which is performed by the first detection device will be described below. The first detection device sets the application voltage Vm of the gas sensor 30 to an oxygen concentration detection voltage Vaf which will be described later and acquires the output current Im at that time as an output current Iaf2. The output current Iaf2 is a current which changes depending on the concentration of oxygen in an exhaust gas (a sample gas) discharged from the internal combustion engine 10.

As will be described later in detail, the first detection device steps up or steps down the application voltage Vm (that is, performs an application voltage sweep), and acquires the output current Im when the application voltage Vm matches a reoxidation current detection voltage Vsen in a period in which the application voltage Vm is stepped down as a reoxidation current Is2. As will be described later, the reoxidation current Is2 has a value which changes depending on the concentration of SOx in the exhaust gas and the concentration of oxygen. Then, the first detection device calculates a difference between the output current Iaf2 and the reoxidation current Is2 as a parameter Ia2. The parameter Ia2 has a value which changes depending on the concentration of SOx in the exhaust gas but in which an influence of the concentration of oxygen is removed. The first detection device detects the concentration of SOx in the exhaust gas based on the parameter Ia2.

The parameter Ia2 is affected by individual characteristics differences between the gas sensors 30. Therefore, the first detection device acquires a parameter Ia1 indicating the individual characteristic differences between the gas sensors 30 as will be described later and calculates a difference between the parameter Ia2 and the parameter Ia1 as a SOx detection parameter Id. The first detection device determines whether SOx with a predetermined concentration (a threshold concentration) or higher is contained in the exhaust gas (whether there is SOx with a predetermined concentration or higher contained in the exhaust gas) using the SOx detection parameter Id. An arbitrary concentration greater than 0% which corresponds to a desired detection level is selected as the predetermined concentration (the threshold concentration).

Details of Operation (Detection of an Output Current Indicating a Concentration of Oxygen and the Concentration of Oxygen)

An operation of the first detection device when the "output current Iaf2 which is a current changing depending on the concentration of oxygen in the exhaust gas" is detected will be described below. When the gas sensor 30 enters a sensor-activated state, the first detection device sets the application voltage Vm to an oxygen concentration detection voltage Vaf (for example, 0.3 V) such that the first electrode 41a has a low potential and the second electrode 41b has a high potential to detect the output current Iaf1. That is, the first electrode functions as a negative electrode and the second electrode 41b functions as a positive electrode. The oxygen concentration detection voltage Vaf is set to a voltage which is equal to or higher than a voltage (a decomposition start voltage) at which decomposition of oxygen ($O_2$) in the first electrode 41a is started, which is a voltage at which a limiting current of oxygen which will be described later is observed, and which is a voltage lower than a decomposition start voltage of oxygen-containing components other than oxygen. Accordingly, oxygen contained in the exhaust gas is reductively decomposed into oxide ions ($O^{2-}$) in the first electrode 41a.

The oxide ions are transmitted to the second electrode 41b via the solid electrolyte 41s and are changed to oxygen ($O_2$), which is discharged to the atmosphere via the air introduction passage SP2. As described above, the migration of oxygen due to transmission of oxide ions from the negative electrode (the first electrode 41a) to the positive electrode (the second electrode 41b) via the solid electrolyte 41s is referred to as an "oxygen pumping effect."

Due to the transmission of oxide ions due to the oxygen pumping effect, a current flows between the first electrode 41a and the second electrode 41b. The current flowing between the first electrode 41a and the second electrode 41b is referred to as an "output current Im (or an electrode current Im)." In general, the output current Im has a trend of increasing as the application voltage Vm increases. However, since a flow rate of the exhaust gas reaching the first electrode 41a is limited by the diffusion resistor portion 61, a consumption rate of oxygen due to the oxygen pumping effect is higher than a feed rate of oxygen to the first electrode 41a. That is, the reductive decomposition reaction of oxygen in the first electrode 41a (the negative electrode) is in a diffusion rate controlled state.

When the reductive decomposition reaction of oxygen in the first electrode 41a is in the diffusion rate controlled state, the output current Im does not increase but is substantially constant in spite of an increase of the application voltage Vm. Such characteristics are referred to as "limiting current characteristics." A range of the application voltage in which the limiting current characteristics are exhibited (observed) is referred to as a "limiting current region." The output current Im in the limiting current region is referred to as a "limiting current." The magnitude of the limiting current for oxygen (a limiting current value) corresponds to a feed rate of oxygen to the first electrode 41a (the negative electrode). Since the flow rate of the exhaust gas reaching the first electrode 41a is kept constant by the diffusion resistor portion 51 as described above, the feed rate of oxygen to the first electrode 41a corresponds to the concentration of oxygen contained in the exhaust gas.

Accordingly, in the gas sensor 30, the output current (the limiting current) Im when the application voltage Vm is set to a "predetermined voltage (for example, 0.3 V) in the limiting current region of oxygen" corresponds to the concentration of oxygen contained in the exhaust gas. The first detection device acquires the limiting current Im as an "output current Iaf2 indicating the concentration of oxygen in the exhaust gas."

An air-fuel ratio A/F of the engine and a concentration of oxygen in the exhaust gas have a one-to-one correspondence relationship. Accordingly, the first detection device may store a relationship between the limiting current Im of oxygen and the air-fuel ratio A/F of the engine in a ROM in advance and may acquire the air-fuel ratio A/F of the engine based on the relationship and the detected limiting current Im of oxygen.

Detection Principle and Detection Method in SOx Concentration Detection

A detection principle and a detection method of a concentration of SOx in an exhaust gas (a sample gas) will be described below. SOx concentration detection in this specification refers to any one of acquiring a SOx concentration detection parameter indicating a concentration of SOx contained in the exhaust gas, detecting (measuring) the concentration of SOx contained in the exhaust gas using the SOx concentration detection parameter, and determining whether SOx with a predetermined concentration or higher is contained in the exhaust gas using the SOx concentration detection parameter.

The above-mentioned oxygen pumping effect also occurs for oxygen-containing components such as "SOx (sulfur oxides) and $H_2O$ (water)" containing an oxygen atom in a molecule. That is, when a voltage equal to or higher than the decomposition start voltages of the compounds is applied across the first electrode 41a and the second electrode 41b, the compounds are reductively decomposed to produce oxide ions. The oxide ions are transmitted from the first electrode 41a to the second electrode 41b due to the "oxygen pumping effect." Accordingly, an output current Im flows between the first electrode 41a and the second electrode 41b.

However, the concentration of SOx contained in the exhaust gas is very low and a current due to decomposition of SOx is also very small. A current due to decomposition of oxygen-containing components (such as water and carbon dioxide) other than SOx also flows between the first electrode 41a and the second electrode 41b. Accordingly, it is difficult to accurately detect only the output current due to SOx.

Therefore, from the results of intensive research, the inventor of the disclosure acquired the knowledge that it is possible to accurately detect the SOx concentration by performing an application voltage sweep using a step-up sweep and a "step-down sweep at a predetermined sweeping rate" as one cycle at the time of detecting the SOx concentration.

The step-up sweep is a process of slowly stepping up the application voltage Vm from a lower limit voltage Va1 to an upper limit voltage Va2. The step-down sweep is a process of slowly stepping down the application voltage Vm from the upper limit voltage Va2 to the lower limit voltage Va1. The lower limit voltage Va1 and the upper limit voltage Va2 are the potential of the second electrode 41b relative to the potential of the first electrode 41a and have a positive voltage value.

The lower limit voltage Va1 is set to a voltage in a voltage range (hereinafter also referred to as a "first voltage range") which is lower than a decomposition start voltage of SOx (about 0.6 V) and higher than a minimum value of the application voltage in the limiting current region of oxygen. Since the minimum value of the application voltage in the limiting current region of oxygen depends on the air-fuel ratio A/F of the engine, a lower limit value of the first voltage range may be changed depending on the air-fuel ratio A/F of the engine. Specifically, the lower limit value of the first voltage range is a voltage in a range of 0.2 V to 0.45 V and an upper limit value of the first voltage range is 0.6 V, for example. That is, the lower limit voltage Va1 is selected in a range equal to or higher than 0.2 V and lower than 0.6 V.

The upper limit voltage Va2 is set to a voltage in a voltage range (hereinafter also referred to as a "second voltage range") which is higher than the decomposition start voltage of SOx (about 0.6 V) and lower than an upper limit value (2.0 V) of a voltage at which the solid electrolyte 41s does not break down. That is, the upper limit voltage Va2 is selected in a range higher than 0.6 V and equal to or lower than 2.0 V.

Figure 3A:
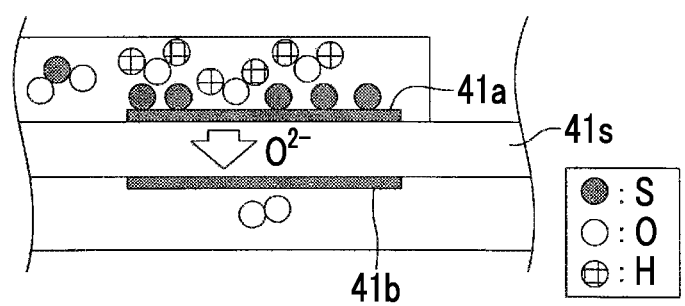
FIG. 3A is a diagram schematically illustrating a decomposition reaction of SOx which occurs in the element portion.

In a period in which the step-up sweep is performed, when the application voltage Vm applied across the first electrode 41a and the second electrode 41b becomes equal to or higher than the decomposition start voltage of SOx, SOx contained in the exhaust gas is reductively decomposed into S and $O^{2-}$ in the first electrode 41a (the negative electrode) as illustrated in FIG. 3A.

As a result, a reductive decomposition product (S (sulfur)) of SOx is adsorbed on the first electrode 41a (the negative electrode).

Figure 3B:
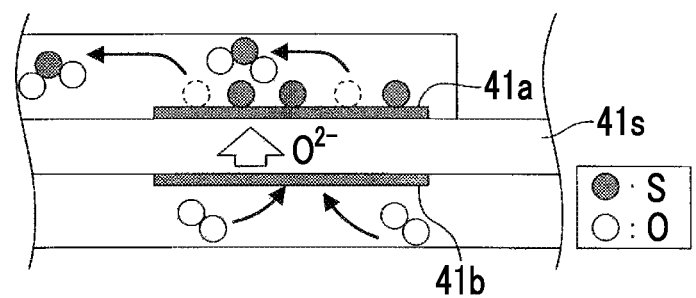
FIG. 3B is a diagram schematically illustrating a reoxidation reaction of sulfur which occurs in the element portion.

In a period in which the step-down sweep is performed, when the application voltage Vm becomes lower than the decomposition start voltage of SOx, a reaction in which S and $O^2$ adsorbed on the first electrode 41a (the negative electrode) react with each other to produce SOx (hereinafter also referred to as a "reoxidation reaction of S (sulfur)") occurs as illustrated in FIG. 3B. At this time, the output current Im changes as will be described later due to the "reoxidation reaction of S." The change of the output current Im due to the "reoxidation reaction of S" is referred to as a "reoxidation current change."

According to the research of the inventor, it was proved that a reoxidation current change significant for the SOx concentration detection may not appear depending on the sweeping rate of the step-down sweep (a voltage drop per predetermined elapsed time). This will be described below with reference to FIGS. 4A and 4B.

Figure 4A:
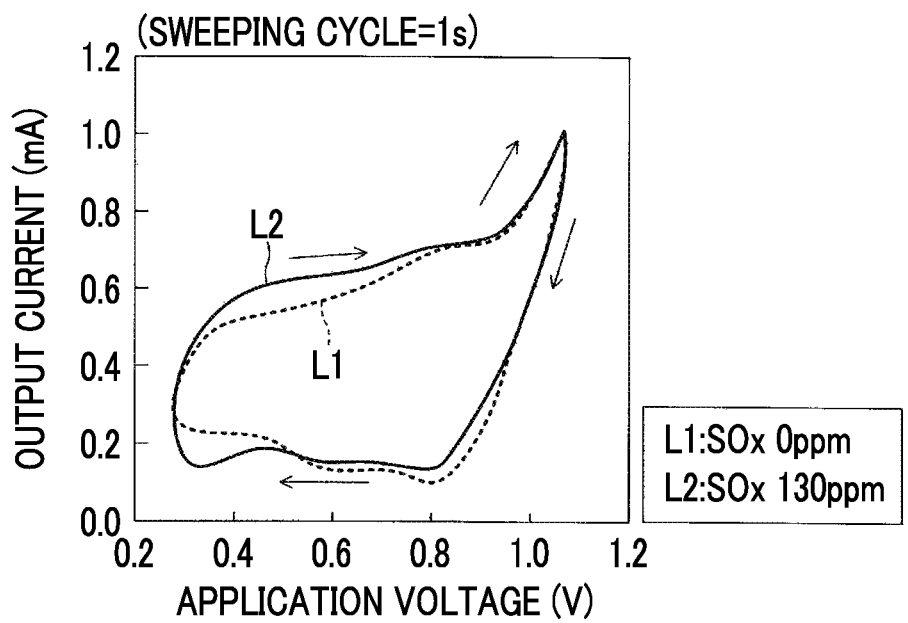
FIG. 4A is a graph illustrating a relationship between an application voltage and an output current.
Figure 4B:
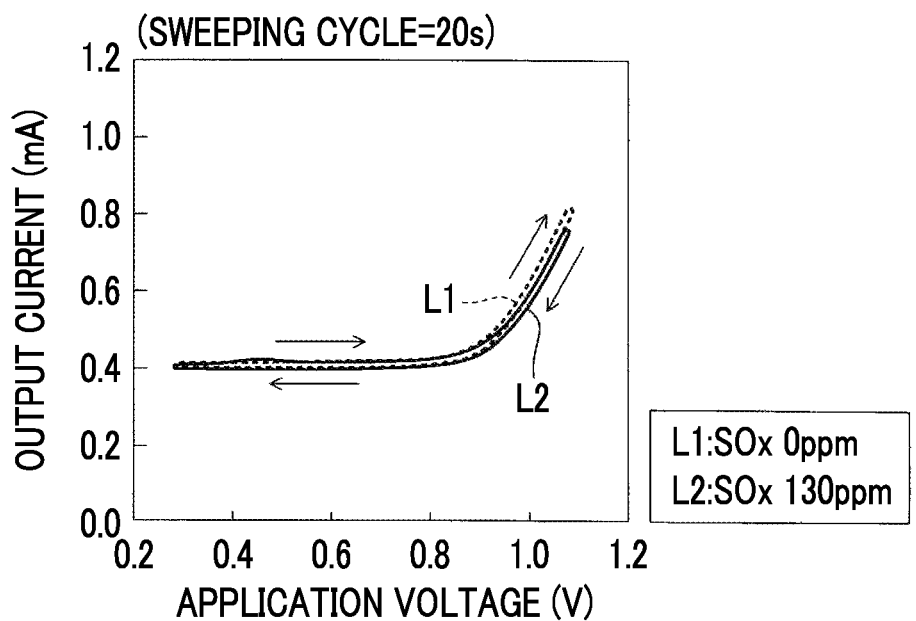
FIG. 4B is a graph illustrating a relationship between an application voltage and an output current.

FIG. 4A is a graph schematically illustrating a relationship between the application voltage Vm and the output current Im when the application voltage sweep is performed with a sweeping cycle time (that is, a sum of a time required for the step-up sweep and a time required for the step-down sweep, a cycle time of the application voltage sweep) set to 1 second. FIG. 4B is a graph schematically illustrating a relationship between the application voltage Vm and the output current Im when the application voltage sweep is performed at a sweeping rate (with a sweeping cycle time of 20 seconds) which is lower than that in the example illustrated in FIG. 4A. The waveform of the application voltage Vm is a sinusoidal waveform illustrated in FIG. 7B.

In a result of comparison between both examples, a difference (a difference in current value) between the "output current Im when a concentration of SOx in a sample gas is 0 ppm" indicated by a line L1 and the "output current Im when a concentration of SOx in the sample gas is 130 ppm" indicated by a line L2 in a voltage range lower than the decomposition start voltage of SOx (0.6 V) appears more distinctly in the example illustrated in FIG. 4A in which the sweeping rate of the application voltage sweep is higher than that in the example illustrated in FIG. 4B. That is, in the example illustrated in FIG. 4A, a current change (the reoxidation current change) significant for SOx concentration detection appears. The mechanism by which such a phenomenon occurs is thought to be as follows.

That is, when the sweeping rate is set to be lower than a predetermined rate, the reoxidation reaction of S progresses continuously and slowly in the step-down sweep and thus a significant reoxidation current change does not appear. On the other hand, when the sweeping rate is set to be higher than a predetermined sweeping rate, the reoxidation reaction of S does not progress so much and the application voltage Vm decreases in the step-down sweep. When the application voltage Vm becomes a voltage in a "voltage range in which the reoxidation reaction of S is activated," the reoxidation reaction of S progresses rapidly. Accordingly, a current change significant for SOx concentration detection appears.

In this way, depending on the sweeping rate when the step-down sweep is performed, a current change significant for SOx concentration detection may appear or may not appear. Accordingly, in the step-down sweep, it is necessary to set the sweeping rate to a predetermined rate at which a significant current change indicating the reoxidation current change appears. The predetermined rate can be set to an appropriate rate at which a significant current change indicating a reoxidation current change appears by a preliminary experiment.

Figure 7A:
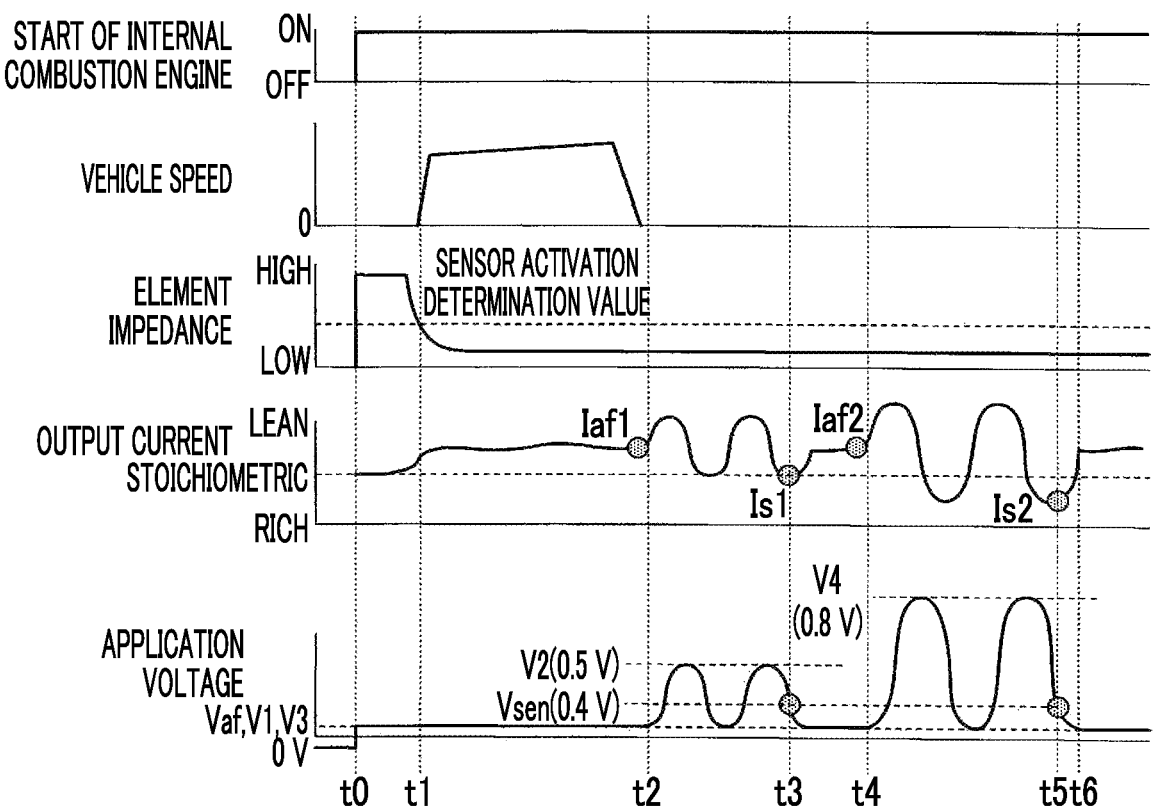
FIG. 7A is a timing chart schematically illustrating an operation of the gas detection device according to the first embodiment of the disclosure.
Figure 7B:
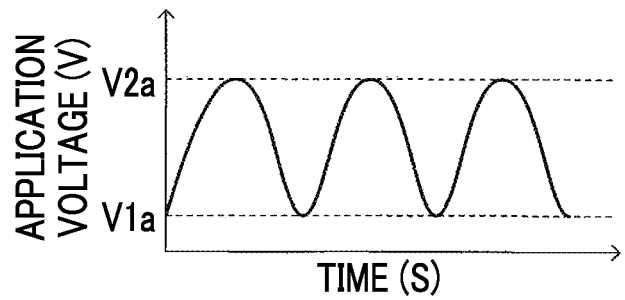
FIG. 7B is a graph illustrating a waveform of an application voltage when SOx detection is performed.

According to an experiment, for example, it was proved that when a voltage of a sinusoidal waveform illustrated in FIG. 7B is applied across the first electrode 41a and the second electrode 41b, the sweeping rate may be set to a rate at which a frequency F in a predetermined range (typically a range of 0.1 Hz to 5 Hz) is obtained. The lower limit value of the frequency F in the predetermined range is determined from a point of view that a signal difference (the reoxidation current change) significant for SOx concentration detection is not obtained when the frequency is lower than the lower limit value. The upper limit value of the frequency F in the predetermined range is determined from a point of view that a degree of contribution from other causes of a current change (specifically, a capacitance of the solid electrolyte 41s or the like) other than the concentration of SOx increases when the frequency is higher than the upper limit value.

Figure 7C:
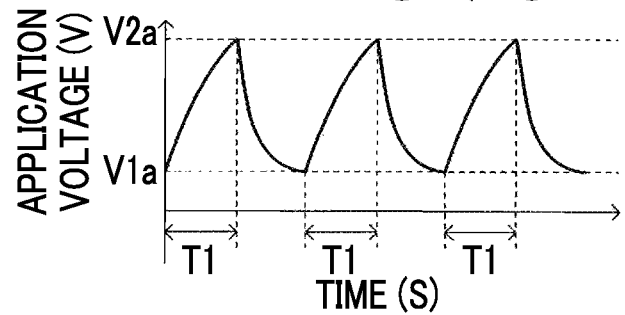
FIG. 7C is a graph illustrating another waveform of an application voltage when SOx detection is performed.

On the other hand, according to an experiment, it was also proved that when a voltage of a non-sinusoidal waveform resulting from charging/discharging of a capacitor is applied across the first electrode 41a and the second electrode 41b as illustrated in FIG. 7C, the sweeping rate may be set to a rate at which a response time constant T1 of a voltage switching waveform is in a predetermined range (typically, a range of 0.1 sec to 5 sec). In this specification, the response time constant T1 is a time required for the application voltage Vm to change from the lower limit voltage Va1 to the upper limit voltage Va2 (or vice versa).

When the predetermined ranges of the frequency F and the response time constant T1 are converted into a time required for the step-down sweep (a time until the application voltage changes from the upper limit voltage Va2 to the lower limit voltage Va1), the predetermined ranges are converted into a range of 0.1 sec to 5 sec. In some embodiments, the time ranges from 0.1 sec to 5 sec.

It was also proved that the "reoxidation current change" mainly depends strongly on a concentration of S in an exhaust gas (a sample gas) as will be described later with reference to FIGS. 5A and 5B. In other words, there is a low likelihood that the reoxidation current change will be affected by a "gas (for example, water) of oxygen-containing components other than sulfur oxides (SOx)" in the exhaust gas. That is, when the step-up sweep is performed, decomposition products (for example, hydrogen which is a decomposition product of water) of "oxygen-containing components other than sulfur oxides" are not adsorbed on the first electrode 41a. Accordingly, a phenomenon that decomposition products of the "oxygen-containing components other than sulfur oxides" undergo a reoxidation reaction in the first electrode 41a and are returned to the oxygen-containing components does not substantially occur in a period in which the step-down sweep is performed. Accordingly, it is possible to accurately detect the concentration of SOx in the exhaust gas using the reoxidation current change.

For example, it is possible to accurately detect a concentration of SOx in the exhaust gas based on the "output current Im when the application voltage Vm becomes a reoxidation current detection voltage Vsen (for example, 0.4 V) which is a voltage lower than the decomposition start voltage of SOx in the step-down sweep (where the output current Im at this time is hereinafter also referred to as a "reoxidation current Is")". FIG. 5A is a graph schematically illustrating a relationship between the application voltage (an application voltage of a sinusoidal waveform) Vm and the output current Im when the application voltage sweep is performed in a state in which the application voltage range and the sweeping rate are set using the same conditions while changing a concentration of SOx contained in an exhaust gas (a sample gas) to various values with an air-fuel ratio of the engine kept constant. From the example illustrated in FIG. 5A, it can be seen that the output current Im (that is, the reoxidation current Is) at the reoxidation current detection voltage Vsen (=0.4 V) decreases as the concentration of SOx in the exhaust gas increases. In this way, the reoxidation current Is is a parameter indicating the reoxidation current change of SOx.

Figure 5A:
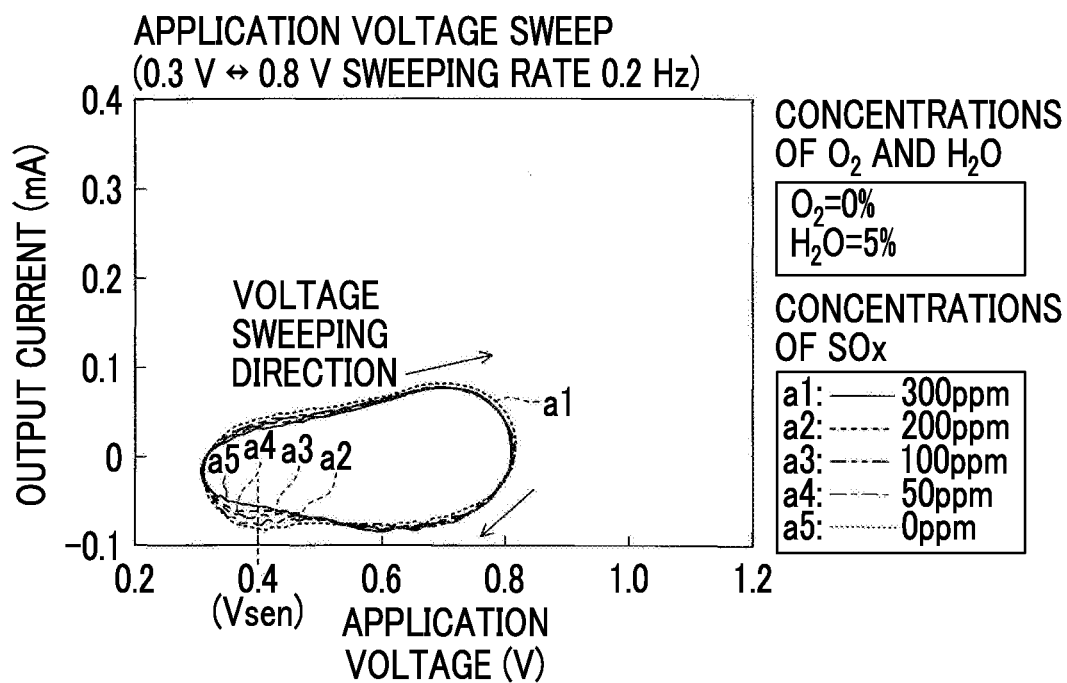
FIG. 5A is a graph illustrating a relationship between an application voltage and an output current when a concentration of SOx in an exhaust gas (a sample gas) changes variously.
Figure 5B:
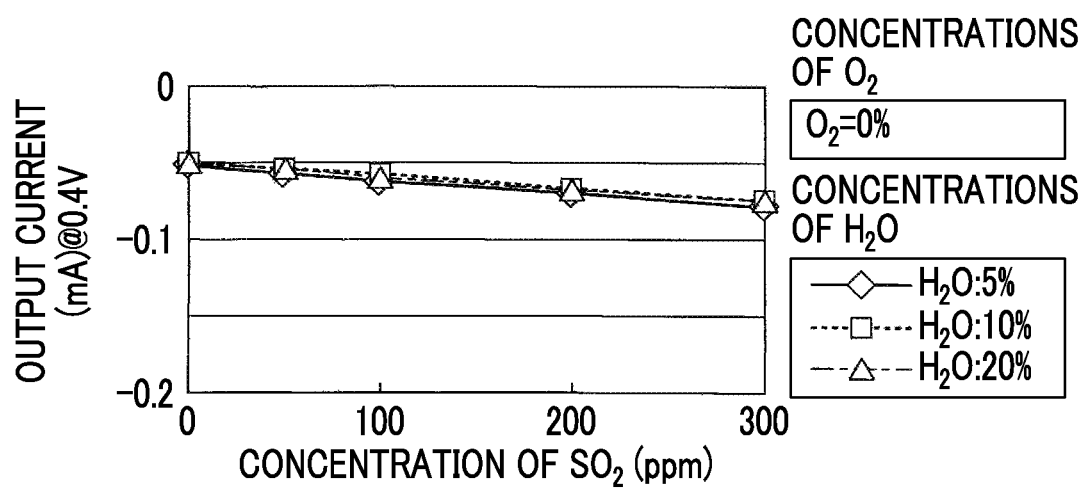
FIG. 5B is a graph illustrating a relationship between voltage concentration of SOx ($SO_2$) and an output current when a concentration of $H_2O$ in an exhaust gas (a sample gas) changes variously.

FIG. 5B is a graph schematically illustrating a relationship between the concentration of SOx and the output current Im (that is, the reoxidation current Is) at the reoxidation current detection voltage Vsen when the application voltage sweep is performed under the same conditions as in FIG. 5A while changing a concentration of $H_2O$ contained in an exhaust gas (a sample gas) to various values. From the example illustrated in FIG. 5B, it can be seen that the output current Im (the reoxidation current Is) at the reoxidation current detection voltage Vsen depends on the concentration of SOx in the exhaust gas but does not depend on the concentration of $H_2O$ in the exhaust gas.

From the above description, it can be understood that it is possible to accurately detect the concentration of SOx in the exhaust gas without being affected by "oxygen-containing components (for example, water) other than SOx" in the exhaust gas using the reoxidation current change."

On the other hand, the magnitude of the output current Im (the reoxidation current Is) at the reoxidation current detection voltage Vsen changes depending on the concentration of oxygen contained in the exhaust gas. This is because the output current Im includes a current component due to migration of oxide ions ($O^{2-}$) which are produced by reductive decomposition of oxygen contained in the exhaust gas. Therefore, the first detection device detects the output current Iaf based on oxygen contained in the exhaust gas immediately before the application voltage sweep for acquiring the reoxidation current Is is started, and acquires a value, which is obtained by subtracting the output current Iaf from the reoxidation current Is acquired thereof, as a SOx detection parameter.

Figure 6:
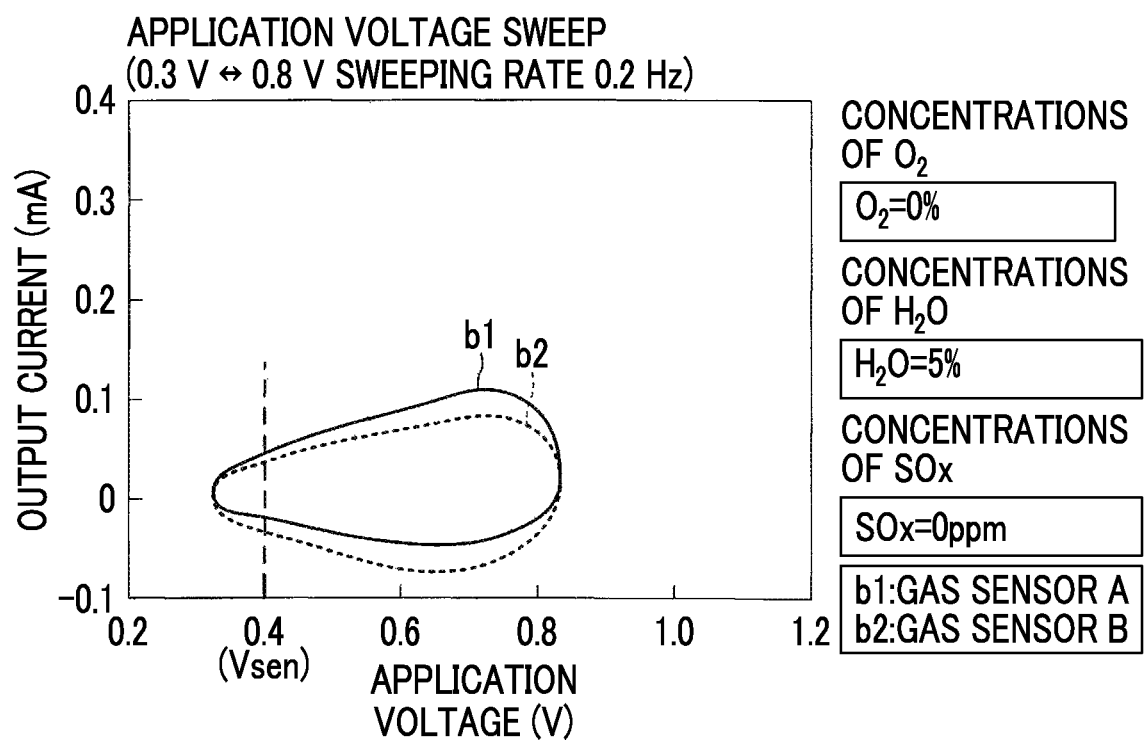
FIG. 6 is a graph illustrating a relationship between an application voltage and an output current for two different gas sensors.

As a result of further research of the inventor of the disclosure, it was proved that output currents Im acquired when one cycle of an application voltage sweep is performed under the same experiment conditions using gas sensor A and gas sensor B which are the same type of gas sensors (the gas sensor 30) may exhibit different output current characteristics (application voltage-output current characteristics) as illustrated in FIG. 6. Such a difference in the output current characteristics is thought to result from individual differences between the gas sensors 30 (differences in individual characteristics between the gas sensors 30). Specifically, individual differences between the gas sensors 30 includes the following.

A difference (unevenness) in an area of the first electrode 41a and an area of the second electrode 41b between the gas sensors 30

A difference (unevenness) in a volume of the solid electrolyte 41s between the gas sensors 30

A difference (unevenness) in resistance and capacitance of the solid electrolyte due to aging Due to the individual differences in output current characteristics between the gas sensors 30, the output current Im (the reoxidation current Is) when the application voltage Vm becomes the reoxidation current detection voltage Vsen in the step-down sweep varies between the gas sensors 30 in spite of there being the same concentrations of SOx in the exhaust gas. As a result, the SOx detection parameter varies between the gas sensors 30.

On the other hand, when a final SOx detection parameter is acquired by excluding a current value varying due to individual differences between the gas sensors 30 from the reoxidation current Is (or the SOx detection parameter) and the concentration of SOx is detected using the final SOx detection parameter, it is expected that the concentration of SOx will be able to be more accurately detected regardless of the individual differences between the gas sensors 30. Therefore, the first detection device calculates a difference Id as a SOx detection parameter Id which does not depend on individual differences between the gas sensors 30, and detects the concentration of SOx using the parameter Id.

More specifically, as illustrated in FIG. 7A, at time t0 which is a time point at which the internal combustion engine 10 is started, the first detection device starts control of the heater 71 such that the solid electrolyte 41s is heated by the heater 71. Accordingly, the temperature of the solid electrolyte 41s increases to a predetermined temperature which is equal to or higher than a temperature (hereinafter also referred to as an "activation temperature") at which the solid electrolyte 41s exhibits oxide ion conductivity.

At time t1, when the temperature of the solid electrolyte 41s (a sensor element temperature) is equal to or higher than the activation temperature, an element impedance is lower than a sensor activation determination value and the gas sensor 30 enters a sensor-activated state. Then, the first detection device starts a process of detecting an output current Im (Iaf1) indicating a concentration of oxygen in an exhaust gas. At time t0, the first detection device starts application of the above-mentioned oxygen concentration detection voltage Vaf (specifically, 0.3 V) across the first electrode 41a and the second electrode 41b. When the temperature of the solid electrolyte 41s is equal to or higher than the activation temperature and the application voltage Vm is set to the oxygen concentration detection voltage Vaf, oxygen molecules are decomposed and the oxygen pumping effect is exhibited, but oxygen-containing component gases (which contain SOx) other than oxygen do not decompose.

From time t1, the first detection device continuously detects the output current Im. At time t2, when SOx detection start conditions are satisfied (that is, when the air-fuel ratio A/F of the engine is stable and other conditions which will be described later are satisfied), the first detection device acquires (stores) the output current Im detected immediately before time t2 (that is, the output current Im when the application voltage Vm is set to the oxygen concentration detection voltage Vaf) as a first current Iaf1.

Then, from time t2, the first detection device starts application voltage control for performing a process of detecting a concentration of SOx in the exhaust gas, and performs the process of detecting the concentration of SOx by performing the application voltage control to a time point immediately before time t6.

Specifically, the first detection device performs the application voltage control including at least one cycle (two cycles in this example) of a first application voltage sweep which will be described below, application of an A/F detection voltage of maintaining the application voltage Vm at an A/F detection application voltage Vaf in a predetermined period (one second in this example), and at least one cycle (two cycles in this example) of a second application voltage sweep which will be described below.

That is, the first detection device performs two cycles of the first application voltage sweep from time t2. One cycle of the first application voltage sweep includes a step-up sweep of slowly stepping up the application voltage Vm from the first voltage V1 to the second voltage V2 and a step-down sweep of slowly stepping down the application voltage Vm from the second voltage V2 to the first voltage V1 after the step-up sweep. The step-up sweep of the first application voltage sweep is also referred to as a "first step-up sweep" for the purpose of convenience. The step-down sweep of the first application voltage sweep is also referred to as a "first step-down sweep" for the purpose of convenience. A sweeping voltage range of the first application voltage sweep (that is, a voltage range from the first voltage V1 to the second voltage V2) is referred to as a "first sweeping voltage range."

The first detection device acquires (stores) the output current Im when the application voltage Vm becomes the reoxidation current detection voltage Vsen (=0.4 V) in the second cycle of the first step-down sweep (the second cycle of the first application voltage sweep) (see time t3) as a second current Is1.

Similarly to the above-mentioned lower limit voltage Va1, the first voltage V1 is set to a voltage which is selected in the first voltage range (a range of 0.2 V to 0.6 V). In this example, the first voltage V1 is set to 0.3 V. The second voltage V2 is set to a voltage which is higher than the first voltage V1 and equal to or lower than the decomposition start voltage of SOx. Specifically, the second voltage V2 is set to a voltage which is higher than 0.3 V and equal to or lower than 0.6 V. In this example, the second voltage V2 is set to 0.5 V which is a voltage lower than the decomposition start voltage of SOx. Accordingly, since SOx contained in the exhaust gas is not substantially reductively decomposed into S and $O^{2-}$ in the first step-up sweep, S which is a reductive decomposition product of SOx is not substantially adsorbed on the first electrode 41a. As a result, a "reoxidation reaction of S" in which S and $O^{2-}$ adsorbed on the first electrode 41a react with each other does not occur substantially in the first step-down sweep. Accordingly, the second current Is1 has a value which is not affected by the concentration of SOx in the exhaust gas but is affected by the concentration of oxygen in the exhaust gas and individual differences between the gas sensors 30.

In some embodiments, in order to cause an influence from the individual differences between the gas sensors 30 on the second current Is1 to be equal to or closer to an influence from the individual differences between the gas sensors 30 on a fourth current 1s2 which will be described later, the sweeping rate of the first application voltage sweep may be set to the same as a switching rate of the second application voltage sweep which will be described later. When it is mentioned that the "sweeping rate of the first application voltage sweep" and the "sweeping rate of the second application voltage sweep" are the same, it means that a "sweeping rate of a step-up sweep" (that is, a voltage change per unit time) which is calculated by Equation (1) and a "sweeping rate of a step-down sweep" which is calculated by Equation (2) are the same.

"sweeping rate of step-up sweep"="upper limit voltage−lower limit voltage"÷"time required for change from lower limit voltage to upper limit voltage" Equation (1):

"sweeping rate of step-down sweep"="upper limit voltage−lower limit voltage"÷"time required for change from upper limit voltage to lower limit voltage" Equation (2):

The first sweeping voltage range may be a voltage range in which an influence from SOx in the exhaust gas on the second current Is1 is very small (that is, a voltage range in which a reduction decomposition reaction and a reoxidation reaction of SOx hardly occur). In this case, the second voltage V2 may be set to a voltage which is higher than the first voltage V1 and which is higher by a predetermined value than the decomposition start voltage of SOx. Specifically, the predetermined value is selected in a range greater than 0 V and equal to or less than 0.1 V.

When the first application voltage sweep of the second cycle ends immediately after time t3, the first detection device maintains the application voltage Vm at the oxygen concentration detection voltage Vaf (specifically, 0.3 V) over a predetermined period (one second in this example). Then, the first detection device acquires (stores) the output current Im detected immediately before time t4 at which one second has elapsed from a time point at which the first application voltage sweep ends (that is, the output current Im when the application voltage Vm is equal to the oxygen concentration detection voltage Vaf) as the second current Iaf2.

The first detection device performs two cycles of the second application voltage sweep (an application voltage sweep for detection of a SOx reoxidation current) from time t4. One cycle of the second application voltage sweep includes a step-up sweep of slowly stepping up the application voltage Vm from a third voltage V3 to a fourth voltage V4 and a step-down sweep of slowly stepping down the application voltage Vm from the fourth voltage V4 to the third voltage V3 after the step-up sweep. The step-up sweep of the second application voltage sweep is also referred to as a "second step-up sweep" for the purpose of convenience. The step-down sweep of the second application voltage sweep is also referred to as a "second step-down sweep" for the purpose of convenience. A sweeping voltage range of the second application voltage sweep (that is, a voltage range from the third voltage V3 to the fourth voltage V4) is referred to as a "second sweeping voltage range."

The first detection device acquires (stores) the output current Im when the application voltage Vm becomes the reoxidation current detection voltage Vsen (=0.4 V) in the second cycle of the second step-down sweep (the second cycle of the second application voltage sweep) (see time t5) as a fourth current Is2.

The second application voltage sweep is application voltage control which is performed to acquire a parameter (the fourth current Is2) indicating the reoxidation current change. Accordingly, the third voltage V3 which is a lower limit voltage of the voltage range of the second application voltage sweep is set similarly to the above-mentioned lower limit voltage Va1. The fourth voltage V4 which is an upper limit voltage of the voltage range is set to a voltage higher than the second voltage similarly to the above-mentioned upper limit voltage Va2. Specifically, the third voltage V3 is set to 0.3 V and the fourth voltage is set to 0.8 V. The sweeping rate of the second application voltage sweep is set to the above-mentioned rate (a rate at which the time required for stepping down from the fourth voltage V4 to the third voltage V3 is in a range of 0.1 second to 5 seconds). As a result, the fourth current Is2 has a value depending on the concentration of SOx in the exhaust gas. The fourth current Is2 has a value which is affected by the concentration of oxygen in the exhaust gas and individual differences between the gas sensors 30.

At time t6, when the application voltage control for detecting the concentration of SOx ends, the first detection device restarts the process of detecting the air-fuel ratio A/F of the engine. That is, the first detection device sets the application voltage Vm to an oxygen concentration detection voltage (0.3 V) at time t6.

The first detection device calculates the first parameter Ia1 (=first current Iaf1−second current Is1) by subtracting the second current Is1 from the first current Iaf1. As described above, the second current Is1 does not depend on the concentration SOx in the exhaust gas, but changes due to an influence of the concentration of oxygen in the exhaust gas. On the other hand, a degree of influence from the concentration of oxygen in the exhaust gas on the second current Is1 appears in the first current Iaf1. Accordingly, the first parameter Ia1 which is a difference between the first current Iaf1 and the second current Is1 is not or hardly affected by any of the influence from the concentration of oxygen in the exhaust gas and the influence from the concentration of SOx in the exhaust gas and has a value in which the influence from the individual differences between the gas sensors 30 is reflected.

The first detection device calculates the second parameter Ia2 (=third current Iaf2−fourth current Is2) using the third current Iaf2 and the fourth current Is2. As described above, the fourth current Is2 changes depending on the concentration of SOx in the exhaust gas and the concentration of oxygen in the exhaust gas. On the other hand, a degree of influence of the concentration of oxygen in the exhaust gas on the fourth current Is2 appears in the third current Iaf2. Accordingly, the second parameter Ia2 which is a difference between the third current Iaf2 and the fourth current Is2 has a value which is not or hardly affected by the influence from the concentration of oxygen in the exhaust gas, which changes depending on the concentration of SOx, and in which the influence from individual differences between the gas sensors 30 is reflected.

Therefore, the first detection device calculates a SOx detection parameter (a difference Id (=Ia2−Ia1)) for evaluating the concentration of SOx by subtracting the first parameter Ia1 from the second parameter Ia2. The difference Id has a value from which the individual differences between the gas sensors 30 is removed and the influence of the concentration of oxygen is removed. Accordingly, the difference Id accurately indicates the concentration of SOx in the exhaust gas and thus has a value which can be suitably used as the SOx detection parameter. Therefore, the first detection device performs the concentration of SOx using the SOx detection parameter Id (the difference Id).

As can be understood from the above description, the first detection device detects the concentration of SOx using the SOx detection parameter (the difference Id) from which the influence of the individual characteristics between the gas sensors 30 is substantially removed. Accordingly, it is possible to accurately detect the concentration of SOx.

Figure 8A:
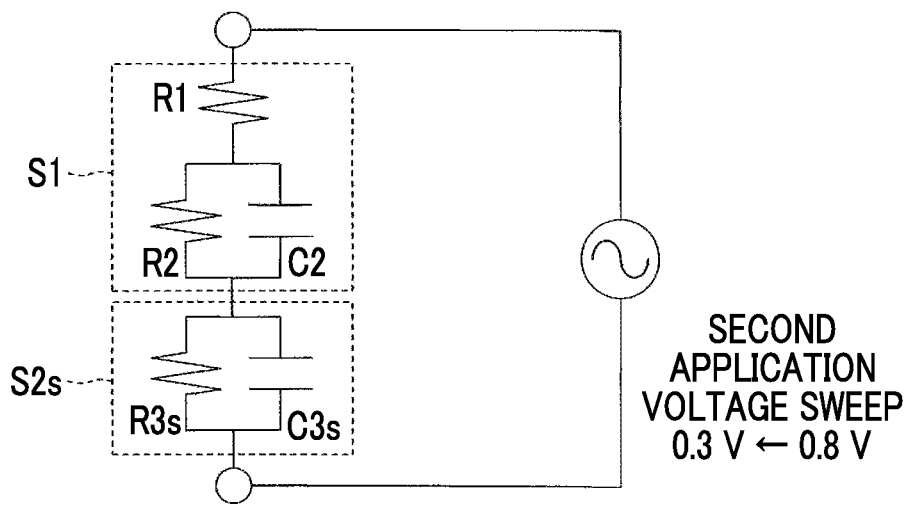
FIG. 8A is a circuit diagram illustrating an equivalent circuit of a gas sensor.
Figure 8B:
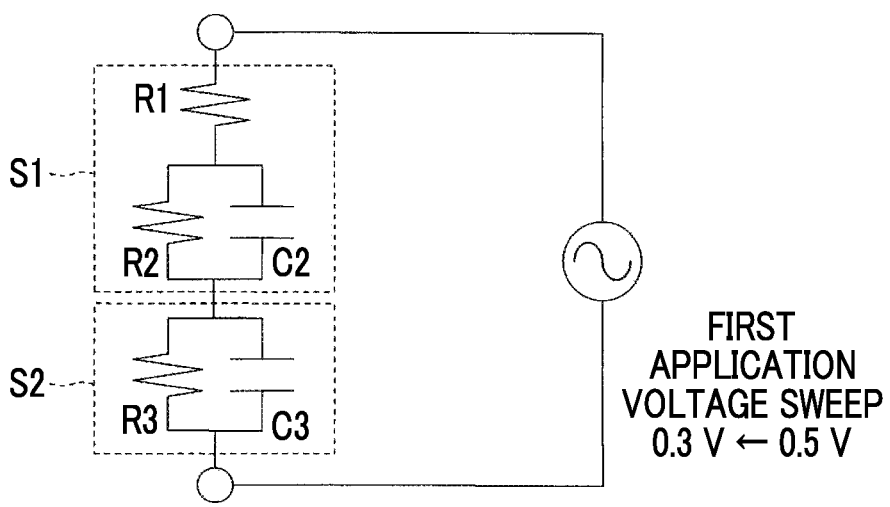
FIG. 8B is a circuit diagram illustrating an equivalent circuit of a gas sensor.

The reason why the SOx detection parameter accurately indicates the concentration of SOx will be additionally described below using an equivalent circuit of the gas sensor 30. FIG. 8A illustrates an equivalent circuit of the gas sensor 30 when the second application voltage sweep is performed, and FIG. 8B illustrates an equivalent circuit of the gas sensor 30 when the first application voltage sweep is performed. Resistance R1 of block S1 in FIGS. 8A and 8B denotes a bulk resistance of the solid electrolyte of the gas sensor 30, resistance R2 denotes a resistance of grain boundary of the solid electrolyte, and capacitance C2 denotes a capacitance of a grain boundary of the solid electrolyte of the gas sensor 30. Resistance R3$s$ of block S2$s$ in FIG. 8A denotes a resistance of an electrode interface and capacitance C3$s$ of block S2$s$ denotes a capacitance of an electrode interface. Similarly, resistance R3 of block S2 in FIG. 8B denotes a resistance of an electrode interface and capacitance C3 of block S2 denotes a capacitance of an electrode interface.

Figure 9:
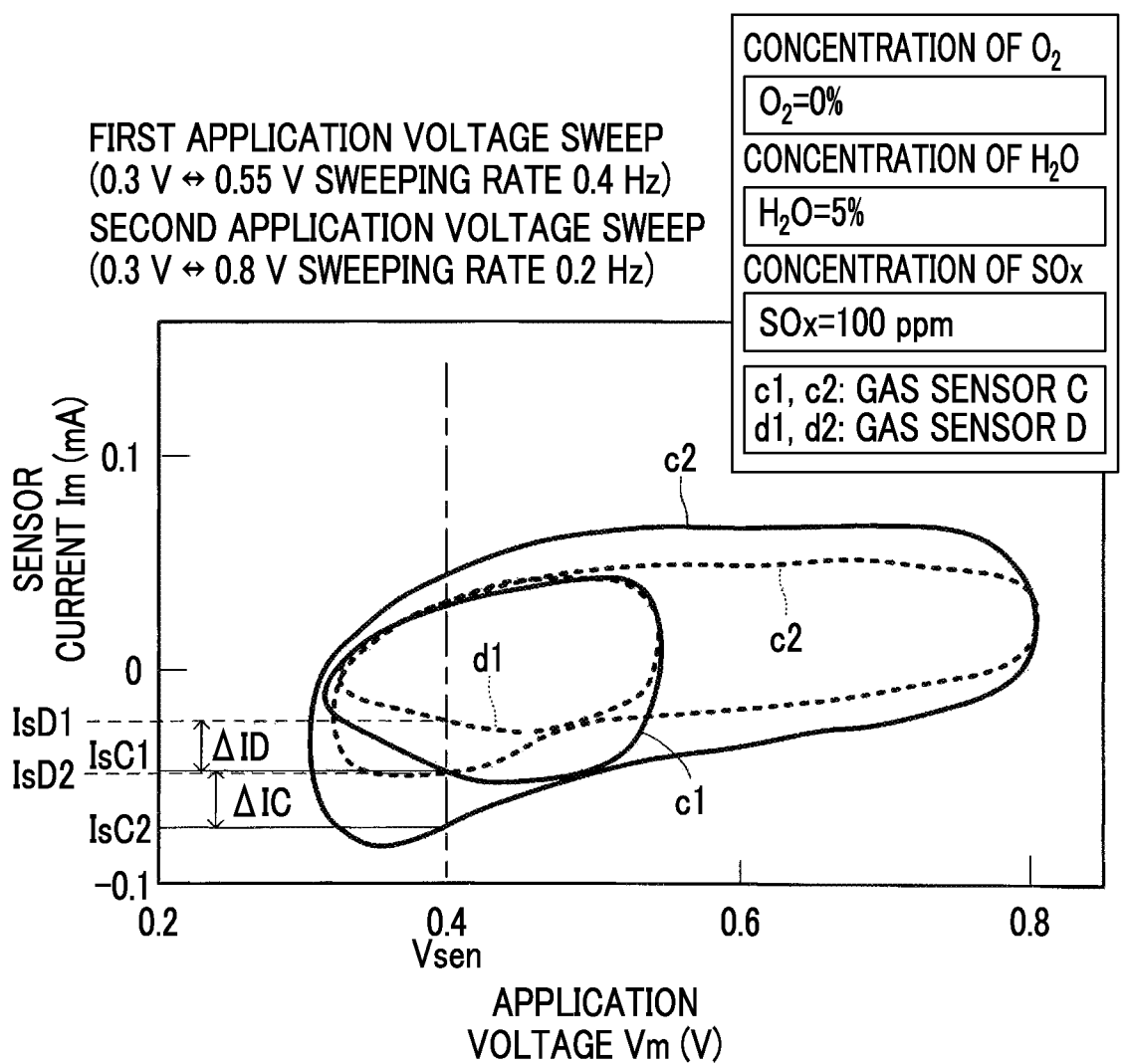
FIG. 9 is a graph illustrating a relationship between an application voltage and an output current in each of a case in which a first application voltage sweep is performed and a case in which a second application voltage sweep is performed.

When the second application voltage sweep is performed, an output current Im2 indicated by a line c2 or d2 in FIG. 9 is observed. The output current Im2 can be considered to be observed due to superimposition of two current components (Im2$a$ and Im2$b$) which will be described below.

Output Current Component Im2$a$

The output current component Im2$a$ is an output current component due to the individual characteristics of the gas sensors 30. Specifically, the output current component Im2$a$ is an output current component which changes due to "resistance R1, resistance R2, and capacitance C2" of block S1 in FIG. 8A.

Output Current Component Im2$b$

The output current component Im2$b$ is an output current component due to an electrode interface which is affected by a decomposition reaction of SOx, adsorption of S on an electrode, a reoxidation reaction of S, and the like (which are hereinafter referred to as "SOx reaction and the like"). Specifically, the output current component Im2$b$ is an output current component which changes due to "resistance R3$s$ and capacitance C3$s$" of block S2$s$ in FIG. 8A.

On the other hand, when the application voltage sweep is performed in a state in which the sweeping rate is set to be substantially the same as in the second application voltage sweep and the sweeping voltage range from the lower limit voltage of the application voltage weep to the upper limit voltage is set to be different from that in the second application voltage sweep, an output current having current characteristics different from the output current Im2 is observed. In this case, the output current component Im2$a$ due to the individual characteristics of the gas sensor 30 (that is, resistance R1, resistance R2, and capacitance C2 of block S1) does not change substantially. However, the state of the electrode interface changes due to an influence of the SOx reaction and the like. Accordingly, the output current component Im2$b$ due to the electrode interface changes depending on the change of the electrode interface (that is, a change from resistance R3 to resistance R3$s$ and a change from capacitance C3 to capacitance C3$s$). This is thought to be the reason why the output current having characteristics different from the output current Im2 is observed.

Accordingly, when the first application voltage sweep is performed at substantially the same sweeping rate as in the second application voltage sweep and in the first sweeping voltage range different from the second sweeping voltage range, an output current Im1 in which the following output current components Im1$a$ and Im1$b$ are superimposed is obtained. The first sweeping voltage range is a voltage range in which the influence of the SOx reaction and the like on the electrode interface is substantially removed or is very small (that is, a voltage range in which a reductive decomposition reaction and a reoxidation reaction of SOx hardly occur).

Output Current Component Im1$a$

The output current component Im1$a$ is an output current component due to the individual characteristics of the gas sensor 30. Specifically, the output current component Im1$a$ is an output current component which changes due to "resistance R1, resistance R2, and capacitance C2" of block S1 in FIG. 8B and is substantially the same as the output current component Im2a.

Output Current Component Im1b

The output current component Im1b is an output current component due to an electrode interface which is not affected by the SOx reaction and the like. Specifically, the output current component Im1b is an output current component which changes due to "resistance R3 and capacitance C3" of block S2 in FIG. 8B.

As can be understood from the above description, it is possible to extract the "output current component due to an electrode interface which is affected by only the SOx reaction and the like" using the output current Im2 and the output current Im1. That is, since an equation ID=Im2−Im1= (Im2a+Im2b)−(Im1a+Im1b)=Im2b−Im1b is established, the difference Id between the output current Im2 and the output current Im1 has a value in which the output current component due to the individual characteristics of the gas sensor 30 (resistance R1, resistance R2, and capacitance C2) is substantially removed and can be considered to be an "output current component due to an electrode interface which is affected by only the SOx reaction and the like."

Accordingly, the difference Id (=Ia2−Ia1) between the second parameter Ia2 which is acquired based on the output current Im2 and from which the influence of the concentration of oxygen is removed and the first parameter Ia1 which is acquired based on at least the output current Im and from which the influence of the concentration of oxygen is removed is a parameter from which the influence of the individual characteristics of the gas sensor 30 is substantially removed and which accurately indicates the concentration of SOx.

The graph illustrated in FIG. 9 represents results of an experiment which has been performed using gas sensor C and gas sensor D of the same type as the gas sensor 30 in order to confirm the above-mentioned points. In this experiment, the concentration of oxygen was 0% and the concentration of water was kept constant (5%). Accordingly, it is not necessary to consider influences of the concentration of oxygen and the concentration of water on the reoxidation current Is.

In FIG. 9, the curves are as follows.

Solid line c1: an output current when the first application voltage sweep was performed on gas sensor C Solid line c2: an output current when the second application voltage sweep was performed on gas sensor C Dashed line d1: an output current when the first application voltage sweep was performed on gas sensor D Dashed line d2: an output current when the second application voltage sweep was performed on gas sensor D Referring to FIG. 9, the output current Im (that is, the reoxidation current) at the reoxidation current detection voltage Vsen (0.4 V) in the second step-down sweep is a reoxidation current IsC2 for gas sensor C and is a reoxidation current IsD2 for gas sensor D. The magnitude of a difference therebetween (=|IsD2−IsC2|) is large.

On the other hand, the output current Im at the reoxidation current detection voltage Vsen in the first step-down sweep is a current IsC1 for gas sensor C and is a current IsD1 for gas sensor D. Accordingly, it can be understood that a current difference dIC for gas sensor C(=IsC1−IsC2) and a current difference dID for gas sensor D (=IsD1−IsD2) have substantially the same value. From the above description, it can be seen that the SOx detection parameter Id (the difference Id) is a parameter from which the influence of the individual characteristics of the gas sensor 30 is substantially removed and which accurately indicates the concentration SOx in the exhaust gas. Accordingly, the first detection device can accurately detect the concentration of SOx using the SOx detection parameter Id.

Specific Operation

A specific operation of the first detection device will be described below. The CPU of the ECU 20 (hereinafter simply referred to as a "CPU") performs routines illustrated in the flowcharts of FIGS. 10 to 14 at predetermined time intervals.

Values of the following flags which are used in these routines are set to "0" in an initial routine which is performed by the CPU when an ignition key switch (not illustrated) which is mounted in the vehicle is changed from an OFF position to an ON position.

Sensor Activation Flag Xact

A sensor activation flag Xact represents that the gas sensor 30 is in a "sensor-activated state" by a value of "1" thereof. The sensor activation flag Xact represents that the gas sensor 30 is not in the "sensor-activated state" (but in a sensor-inactivated state) by a value of "0" thereof.

First Acquisition Completion Flag Xa1

A first acquisition completion flag Xa1 represents that acquisition of the "first current Iaf1 and the second current Is1" which are required for calculating the first parameter Ia1 at the current time point has been completed by a value of "1.". The first acquisition completion flag Xa1 represents that acquisition of at least one of the "first current Iaf1 and the second current Is1" at the current time point has not been completed by a value of "0."

Second Acquisition Completion Flag Xa2

A second acquisition completion flag Xa2 represents that acquisition of the "third current Iaf2 and the fourth current Is2" which are required for calculating the second parameter Ia2 at the current time point has been completed by a value of "1.". The second acquisition completion flag Xa2 represents that acquisition of at least one of the "third current Iaf2 and the fourth current Is2" at the current time point has not been completed by a value of "0."

First Sweep Execution Flag Xsw1

A first sweep execution flag Xsw1 represents that the first application voltage sweep is performed at the current time point by a value of "1." The first sweep execution flag Xsw1 represents that the first application voltage sweep Is not performed at the current time point by a value of "0."

Second Sweep Execution Flag Xsw2

A second sweep execution flag Xsw2 represents that the second application voltage sweep is performed at the current time point by a value of "1." The second sweep execution flag Xsw2 represents that the second application voltage sweep Is not performed at the current time point by a value of "0."

First Voltage Maintaining Process Completion Flag X1hk

A first voltage maintaining process completion flag X1hk represents that the first voltage maintaining process has been completed at the current time point by a value of "1." The first voltage maintaining process completion flag X1hk represents that a first voltage maintaining process has not been completed at the current time point by a value of "0."

SOx Concentration Detection Completion Flag XSOx

A SOx concentration detection completion flag XSOx represents that SOx concentration detection has been completed at the current time point by a value of "1." The SOx concentration detection completion flag XSOx represents that SOx concentration detection has not been completed at the current time point by a value of "0."

Figure 10:
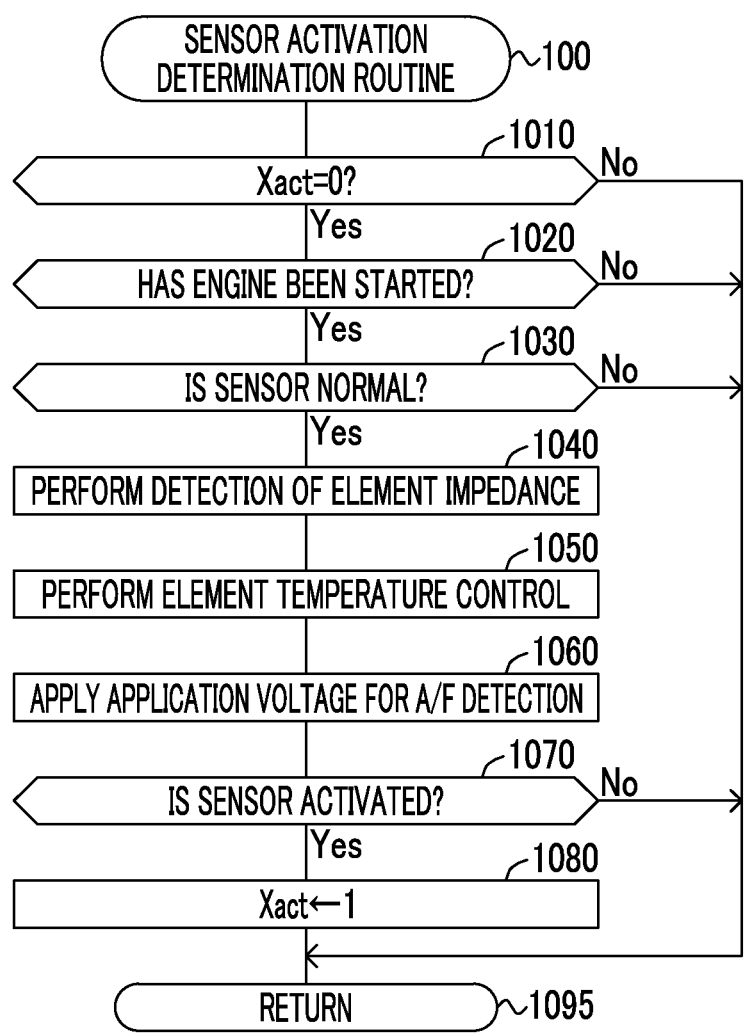
FIG. 10 is a flowchart illustrating a sensor activation determination routine which is performed by a CPU of an ECU illustrated in FIG. 1.

The CPU starts the sensor activation determination routine illustrated in FIG. 10 from Step 1000 at a predetermined time, and determines whether the value of the sensor activation flag Xact is "0" in Step 1010.

Immediately after the ignition key switch is changed to the ON position, the value of the sensor activation flag Xact is "0." In this case, the CPU determines "YES" in Step 1010 and determines whether the engine has been started (whether the internal combustion engine 10 has been started) in Step 1020.

When the engine has been started, the CPU determines "YES" in Step 1020 and determines whether the gas sensor 30 is normal in Step 1030 using a well-known method. For example, when the operation state of the internal combustion engine 10 is changed from a fuel-injecting state to a fuel-cut state during the A/F detection in the previous operation of the internal combustion engine 10 (that is, while setting the application voltage Vm to the oxygen concentration detection voltage Vaf) and the output current Im is not changed, the CPU determines that the gas sensor 30 is abnormal and stores the purport thereof in a backup RAM which can maintain stored details even when the ignition key switch is turned off. In Step 1030 of this routine, the CPU determines whether the gas sensor 30 is normal based on the stored details of the backup RAM.

When the gas sensor 30 is normal, the CPU determines "YES" in Step 1030 and detects an element impedance for element temperature control (internal resistance of the solid electrolyte 41s) based on the output current Im when a voltage (for example, a high-frequency voltage) is applied across the first electrode 41a and the second electrode 41b in Step 1040 (for example, see Japanese Unexamined Patent Application Publication No. H10-232220 (JP H10-232220 A) and Japanese Unexamined Patent Application Publication No. 2002-71633 (JP 2002-71633 A)).

Thereafter, the CPU sequentially performs the processes of Step 1050 and Step 1060 which will be described later and then perform the process of Step 1070. The CPU performs heater power supply control by target impedance feedback (Step 1050). That is, supply of power to the heater 71 is controlled such that the element impedance acquired in Step 1040 as temperature information matches a preset target impedance (for example, see JP 2002-71633 A and Japanese Unexamined Patent Application Publication No. 2009-53108 (JP 2009-53108 A)). The CPU applies the application voltage Vm (specifically, 0.3 V) for detection of an oxygen concentration (that is, for A/F detection) across the first electrode 41a and the second electrode 41b (Step 1060). That is, the CPU sets the application voltage Vm to the oxygen concentration detection voltage Vaf.

In Step 1070, the CPU determines whether the gas sensor 30 is activated (in a sensor-activated state). Specifically, the CPU determines whether the element impedance acquired in Step 1040 is equal to or less than the sensor activation determination value. When the gas sensor 30 is not in the sensor-activated state, the CPU determines "NO" in Step 1070 and temporarily ends this routine in Step 1095.

On the other hand, when the gas sensor 30 is in the sensor-activated state, the CPU determines "YES" in Step 1070 and sets the value of the sensor activation flag Xact to "1" in Step 1080. Thereafter, the CPU temporarily ends this routine in Step 1095.

When the value of the sensor activation flag Xact is not "0" at a time point at which the CPU performs the process of Step 1010, the CPU determines "NO" in Step 1010 and temporarily ends this routine in Step 1095. When the engine has not been started at a time point at which the CPU performs the process of Step 1020, the CPU determines "NO" in Step 1020 and temporarily ends this routine in Step 1095. When the gas sensor 30 is not normal at a time point at which the CPU performs the process of Step 1030, the CPU determines "NO" in Step 1030 and temporarily ends this routine in Step 1095.

SOx detection routine 1 will be described below with reference to FIG. 11. The CPU starts this routine from Step 1100 in FIG. 11 at a predetermined time, and determines whether at least one of the value of the sensor activation flag Xact and the value of the first acquisition completion flag Xa1 is "0" in Step 1105.

SOx detection routine 1 functions substantially when the value of the first acquisition completion flag Xa1 is "0" (when acquisition of the first current Ia1 and the second current Is1 has not been completed) after a time point at which the gas sensor 30 is activated and the value of the sensor activation flag Xact is set to "1."

Accordingly, when the value of the sensor activation flag Xact is not "1" (that is, when the value of the sensor activation flag Xact is "0") or when the value of the first acquisition completion flag Xa1 is "1," the CPU determines "NO" in Step 1105 and temporarily ends this routine in Step 1195.

On the contrary, when the value of the sensor activation flag Xact is set to "1" through the process of Step 1080 in FIG. 10 and the value of the first acquisition completion flag Xa1 is "0," the CPU determines "YES" in Step 1105 and determines whether the value of the first sweep execution flag Xsw1 indicating whether the first application voltage sweep is being performed is "0" in Step 1110.

When the value of the first sweep execution flag Xsw1 is "0," the CPU determines "YES" in Step 1110, calculates the air-fuel ratio A/F of the engine by detecting an oxygen concentration based on the output current Im acquired from the gas sensor 30 and applying the acquired oxygen concentration to a predetermined lookup table (also referred to as a "map") in Step 1115, and then performs Step 1120. When a time point at which the process of Step 1110 is performed is after the first application voltage sweep is performed and the value of the first sweep execution flag Xsw1 is "1" (see Step 1145 which will be described later), the CPU determines "NO" in Step 1110 and directly performs Step 1120.

In Step 1120, the CPU determines whether all the conditions constituting following SOx detection conditions are satisfied based on information acquired from various sensors (such as the NE sensor 21 and the coolant temperature sensor 22). When all of the following conditions are satisfied, the SOx detection conditions are satisfied.

SOx Detection Conditions
 The internal combustion engine 10 is in a warmed-up state (that is, the coolant temperature THW is equal to or higher than a warm-up coolant temperature THWth.).
 The gas sensor 30 is in the sensor-activated state.
 The internal combustion engine is not in a fuel-cut state.
 The air-fuel ratio A/F of the engine is stabilized. That is, an operation state of the internal combustion engine 10 is an idling state or a driving state of the vehicle is a normal traveling state. Whether the operation state of the internal combustion engine 10 is an idling state is determined by determining whether a "state in which the accelerator depression amount AP is "0" and the engine rotation speed NE is equal to or lower than a predetermined rotation speed" is continuously maintained over a predetermined idling time. Whether the driving state of the vehicle is a normal traveling state is determined by determining whether a "state in which a change per unit time of the accelerator depression amount AP is equal to or less than a threshold operation change and a change per unit time of a vehicle speed detected by a vehicle speed sensor which is not illustrated is equal to or lower than a threshold vehicle speed change" is continuously maintained over a predetermined normal traveling threshold time.

Before the ignition key switch is changed to the OFF position after the ignition key switch has been changed from the OFF position to the ON position (that is, after the internal combustion engine 10 is currently started), the SOx concentration detection is not performed at all (the value of the SOx concentration detection completion flag XSOx is not "1").

When the SOx detection conditions are satisfied, the CPU determines "YES" in Step 1120, and determines whether the value of the first sweep execution flag Xsw1 is "0" in Step 1125. As will be described later, when the value of the first sweep execution flag Xsw1 is "1," the first current Iaf1 immediately before the first application voltage sweep is performed (which is used for A/F detection) is already acquired (see Steps 1130 and 1145). Accordingly, when the value of the first sweep execution flag Xsw1 is "0," the first current iaf1 is not acquired yet.

Therefore, when the value of the first sweep execution flag Xsw1 is "0," the CPU determines in "YES" in Step 1125, and acquires the output current Im at that time as the first current Iaf1 (the output current Im when the application voltage Vm is equal to the oxygen concentration detection voltage Vaf) and stores the acquired output current in the RAM in Step 1130. The CPU calculates the air-fuel ratio A/F of the engine by detecting the oxygen concentration based on the acquired first current Iaf1 and applying the oxygen concentration to a predetermined lookup table.

Thereafter, in Step 1135, the CPU determines a first sweeping voltage range (a lower limit voltage (the first voltage V1) and an upper limit voltage (the second voltage V2)), an application voltage sweeping rate, and a reoxidation current detection voltage Vsen of the first application voltage sweep by applying the air-fuel ratio A/F calculated based on the acquired first current Iaf1 to a lookup table M1. Thereafter, the CPU performs Step 1140.

On the other hand, when the value of the first sweep execution flag Xsw1 is not "0" at a time point at which the CPU performs the process of Step 1125, the CPU determines "NO" in Step 1125 and directly performs Step 1140.

In Step 1140, the CPU performs the first application voltage sweep under the sweep conditions (the application voltage sweeping rate and the sweeping voltage range) determined in Step 1135. That is, a process of applying a voltage of a sinusoidal wave corresponding to two periods under the sweep conditions is performed. When the first application voltage sweep is already performed at a time point at which Step 1140 is performed, the CPU continuously performs the application voltage sweep.

Thereafter, in Step 1145, the CPU sets the value of the first sweep execution flag Xsw1 to "1." Then, in Step 1150, the CPU determines whether the current time point is a time point at which the second current Is1 should be acquired. Specifically, the CPU determines whether the application voltage Vm matches the reoxidation current detection voltage Vsen in the first step-down sweep in the second cycle of the first application voltage sweep. When the current time point is a time point at which the second current Is1 should be acquired, the CPU determines "YES" in Step 1150, and acquires the output current Im at that time as the second current Is1 and stores the acquired second current in the RAM in Step 1155. Thereafter, the CPU performs Step 1160.

On the other hand, when the current time point is a time point at which the second current Is1 should be acquired at the time point at which the CPU performs the process of Step 1150, the CPU determines "NO" in Step 1150 and directly performs Step 1160.

In Step 1160, the CPU determines whether two cycles of the first application voltage sweep end.

When two cycles of the first application voltage sweep do not end, the CPU determines "NO" in Step 1160 and temporarily ends this routine in Step 1195. On the other hand, when two cycles of the first application voltage sweep end, the CPU determines "YES" in Step 1160, sequentially performs the processes of Steps 1165 and 1170 which will be described below, and then temporarily ends this routine in Step 1195.

The CPU sets (clears) the value of the first sweep execution flag Xsw1 to "0" (Step 1165). The CPU sets the value of the first acquisition completion flag Xa1 to "1" (Step 1170).

When the SOx detection conditions are not satisfied at a time point at which the process of Step 1120 is performed, the CPU determines "NO" in Step 1120, and sets the application voltage Vm to the oxygen concentration detection application voltage Vaf and sets (clears) both the value of the first sweep execution flag Xsw1 and the value of the first acquisition completion flag Xa1 to "0" in Step 1175. Thereafter, the CPU temporarily ends this routine in Step 1195.

Figure 11:
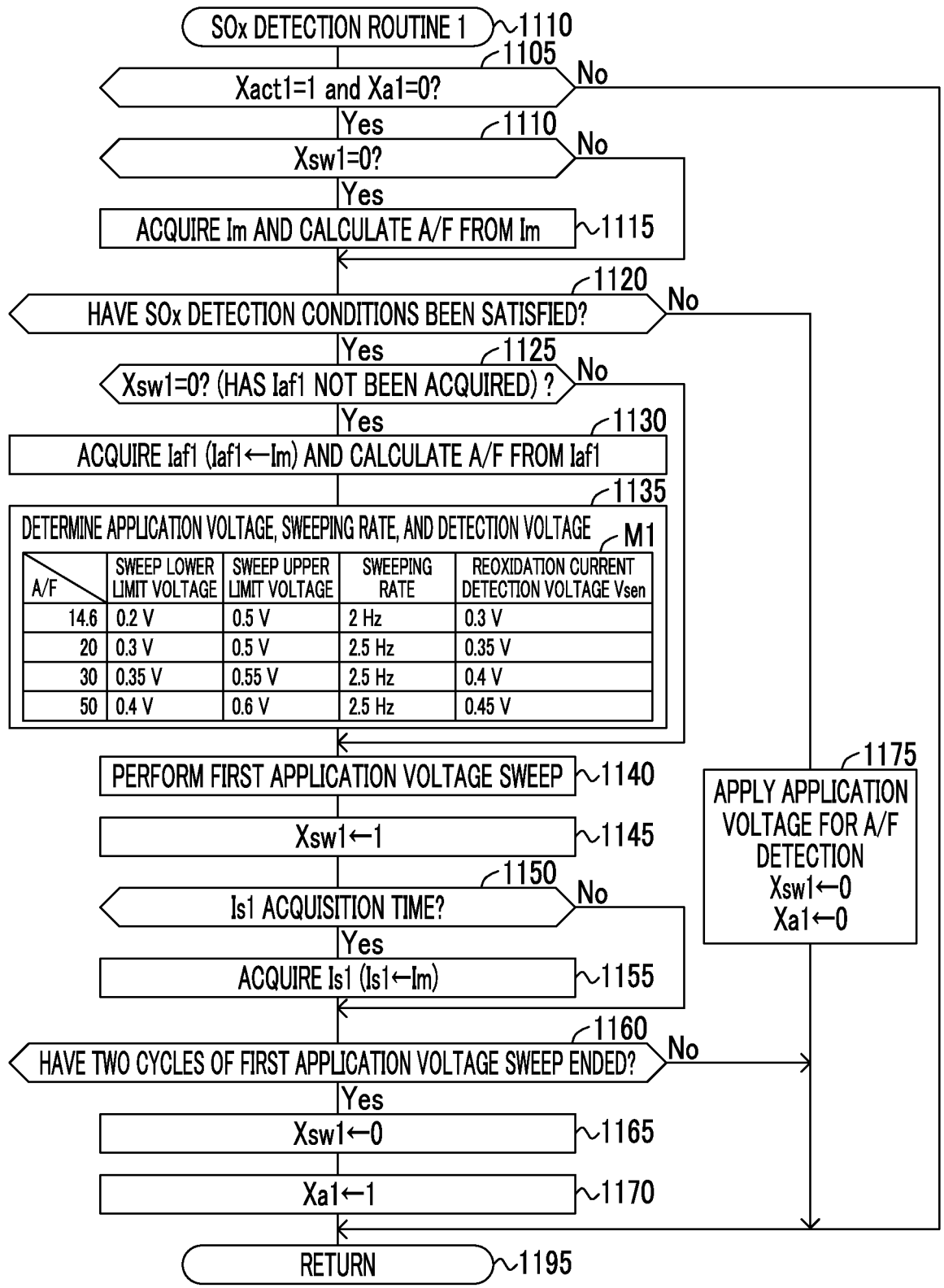
FIG. 11 is a flowchart illustrating SOx detection routine 1 which is performed by the CPU of the ECU illustrated in FIG. 1.

By performing the routine illustrated in FIG. 11, the first current Iaf1 and the second current Is1 are acquired and stored in the RAM.

SOx detection routine 2 will be described below with reference to FIG. 12. The CPU starts this routine from Step 1200 in FIG. 12 at a predetermined time, and determines whether the value of the first acquisition completion flag Xa1 is "1" and the value of the first voltage maintaining process completion flag X1$hk$ is "0" in Step 1210.

SOx detection routine 2 functions substantially when both the output current Ia1 and the output current Is1 are completely acquired, the value of the first acquisition completion flag Xa1 is "1," and the value of the first voltage maintaining process completion flag X1$hk$ is "0."

When the value of the first acquisition completion flag Xa1 is "1" and the value of the first voltage maintaining process completion flag X1$hk$ is "0," the CPU determines "YES" in Step 1210 and sets the application voltage Vm to the oxygen concentration detection (that is, A/F detection) application voltage Vaf (specifically, 0.3 V) in Step 1220.

Thereafter, in Step 1230, the CPU determines whether a timer t1 has a value equal to or greater than a predetermined time t1$th$. The predetermined time t1$th$ is set to an arbitrary value (for example, a value corresponding to one second) greater than 0. The value of the timer t1 is set to "0" in the above-mentioned initial routine.

When the timer t1 has a value less than the predetermined time t1$th$, the CPU determines "NO" in Step 1230 and increases the value of the timer t1 by "1" in Step 1260. Thereafter, the CPU temporarily ends this routine in Step 1295.

On the other hand, when the timer t1 has a value equal to or greater than the predetermined time t1$th$, the CPU determines "YES" in Step 1230, sets the value of the timer t1 to "0" in Step 1240, and then sets the value of the first voltage maintaining process completion flag X1*hk* to "1" in Step 1250. Thereafter, the CPU temporarily ends this routine in Step 1295.

When the value of the first acquisition completion flag Xa1 is "0" or the value of the first voltage maintaining process completion flag X1*hk* is "1" at a time point at which the process of Step 1210 is performed, the CPU determines "NO in Step 1210 and then temporarily ends this routine in Step 1295.

SOx detection routine 3 will be described below with reference to FIG. 13. The CPU starts this routine from Step 1300 in FIG. 13 at a predetermined time, and determines whether the value of the first voltage maintaining process completion flag X1*hk* is "1" and the value of the second acquisition completion flag Xa2 is "0" in Step 1305.

SOx detection routine 3 functions substantially when the value of the second acquisition completion flag Xa2 is "0" after the first voltage maintaining process is completed and the value of the first voltage maintaining process completion flag X1*hk* is "1" (when acquisition of the third current Iaf2 and the fourth current Is2 are not completed).

Accordingly, when the value of the first voltage maintaining process completion flag X1*hk* is not "1" (that is, when the value of the first voltage maintaining process completion flag X1*hk* is "0") or the value of the second acquisition completion flag Xa2 is "1," the CPU determines "NO" in Step 1305 and temporarily ends this routine in Step 1395.

Figure 12:
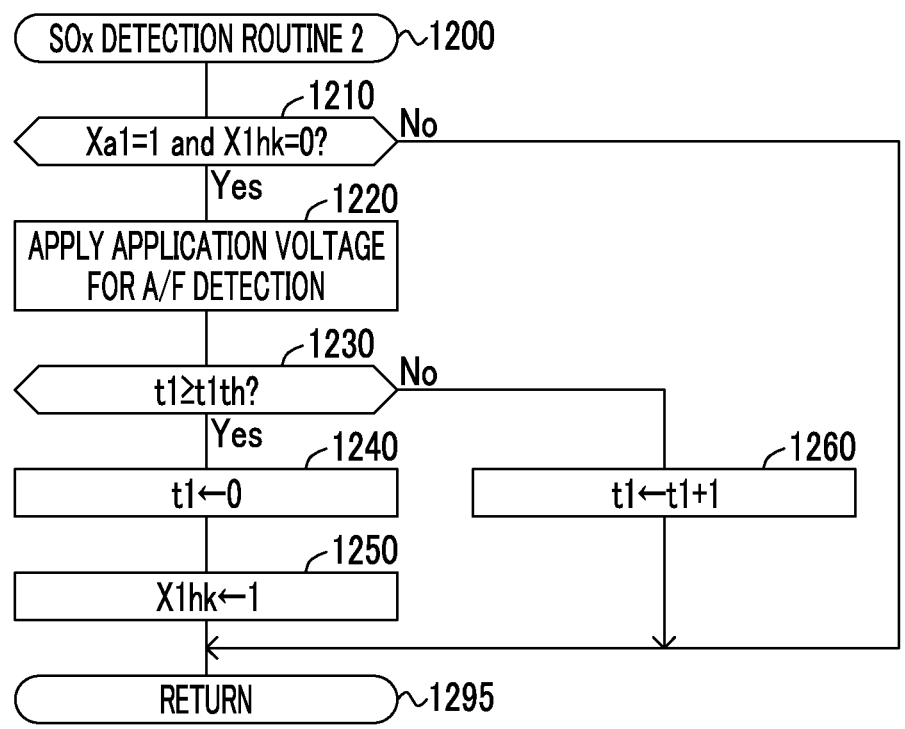
FIG. 12 is a flowchart illustrating SOx detection routine 2 which is performed by the CPU of the ECU illustrated in FIG. 1.

On the other hand, when the value of the first voltage maintaining process completion flag X1*hk* is set to "1" through the process of Step 1250 in FIG. 12 and the value of the second acquisition completion flag Xa2 is "0," the CPU determines "YES" in Step 1305 and then determines whether the value of the second sweep execution flag Xsw2 indicating whether the second application voltage sweep is performed is "0" in Step 1310.

When the value of the second sweep execution flag Xsw2 is "0," the CPU determines "YES" in Step 1310, calculates the air-fuel ratio A/F of the engine by detecting the oxygen concentration based on the output current Im acquired from the gas sensor 30 and applying the oxygen concentration to a predetermined lookup table in Step 1315, and then performs Step 1320. When a time point at which the process of Step 1310 is performed is after performing of the second application voltage sweep is started and the value of the second sweep execution flag Xsw2 is "1" (see Step 1345 which will be described later), the CPU determines "NO" in Step 1310 and then directly performs step 1320.

In Step 1320, the CPU determines whether all the conditions constituting the above-mentioned SOx detection conditions are satisfied based on information acquired from various sensors (such as the NE sensor 21 and the coolant temperature sensor 22).

When the SOx detection conditions are satisfied, the CPU determines "YES" in Step 1320 and determines whether the value of the second sweep execution flag Xsw2 is "0" in Step 1325. As will be described later, when the value of the second sweep execution flag Xsw2 is "1," the second current Iaf2 immediately before the second application voltage sweep is performed (which is used for A/F detection) is already acquired (see Steps 1330 and 1345). Accordingly, when the value of the second sweep execution flag Xsw2 is "0," the second current Iaf2 is not acquired yet.

Therefore, when the value of the second sweep execution flag Xsw2 is "0," the CPU determines "YES" in Step 1325, and acquires the output current Im at that time as the second current Iaf2 (the output current Im when the application voltage Vm is the oxygen concentration detection voltage Vaf) and stores the acquired second current in the RAM in Step 1330. The CPU calculates the air-fuel ratio A/F of the engine by detecting the oxygen concentration based on the acquired second current Iaf2 and applying the oxygen concentration to a predetermined lookup table.

Thereafter, in Step 1335, the CPU determines a voltage range (a lower limit voltage (the third voltage V3) and an upper limit voltage (the fourth voltage V4)), an application voltage sweeping rate, and a reoxidation current detection voltage Vsen of the second application voltage sweep by applying the air-fuel ratio A/F calculated based on the acquired third current Iaf2 to a lookup table M2. Thereafter, the CPU performs Step 1340.

On the other hand, when the value of the second sweep execution flag Xsw2 is not "0" at a time point at which the CPU performs the process of Step 1325, the CPU determines "NO" in Step 1325 and directly performs Step 1340.

In Step 1340, the CPU performs the second application voltage sweep under the sweep conditions (the application voltage sweeping rate and the sweeping voltage range) determined in Step 1335. That is, a process of applying a voltage of a sinusoidal wave corresponding to two periods under the sweep conditions is performed. When the second application voltage sweep is already performed at a time point at which Step 1340 is performed, the CPU continuously performs the application voltage sweep.

Thereafter, in Step 1345, the CPU sets the value of the second sweep execution flag Xsw2 to "1." Then, in Step 1350, the CPU determines whether the current time point is a time point at which the fourth current Is2 should be acquired. Specifically, the CPU determines whether the application voltage Vm matches the reoxidation current detection voltage Vsen during the second step-down sweep in the second cycle of the second application voltage sweep. When the current time point is a time point at which the fourth current Is2 should be acquired, the CPU determines "YES" in Step 1350, and acquires the output current Im at that time as the fourth current Is2 and stores the acquired fourth current in the RAM in Step 1355. Thereafter, the CPU performs Step 1360.

On the other hand, when the current time point is not a time point at which the fourth current Is2 should be acquired at the time point at which the CPU performs the process of Step 1350, the CPU determines "NO" in Step 1350 and directly performs Step 1360.

In Step 1360, the CPU determines whether two cycles of the second application voltage sweep end.

When two cycles of the second application voltage sweep do not end, the CPU determines "NO" in Step 1360 and temporarily ends this routine in Step 1395. On the other hand, when two cycles of the second application voltage sweep end, the CPU determines "YES" in Step 1360, sequentially performs the processes of Steps 1365 and 1370 which will be described below, and then temporarily ends this routine in Step 1395.

The CPU sets (clears) the value of the second sweep execution flag Xsw2 to "0" and sets the value of the second acquisition completion flag Xa2 to "1" (Step 1365). The CPU sets the application voltage Vm to the oxygen concentration detection application voltage Vaf (Step 1370).

When the SOx detection conditions are not satisfied at a time point at which the process of Step 1320 is performed, the CPU determines "NO" in Step 1320, and sets the application voltage Vm to the oxygen concentration detection application voltage Vaf and sets (clears) both the value of the second sweep execution flag Xsw2 and the value of the second acquisition completion flag Xa2 to "0" in Step 1375. Thereafter, the CPU temporarily ends this routine in Step 1395.

Figure 13:
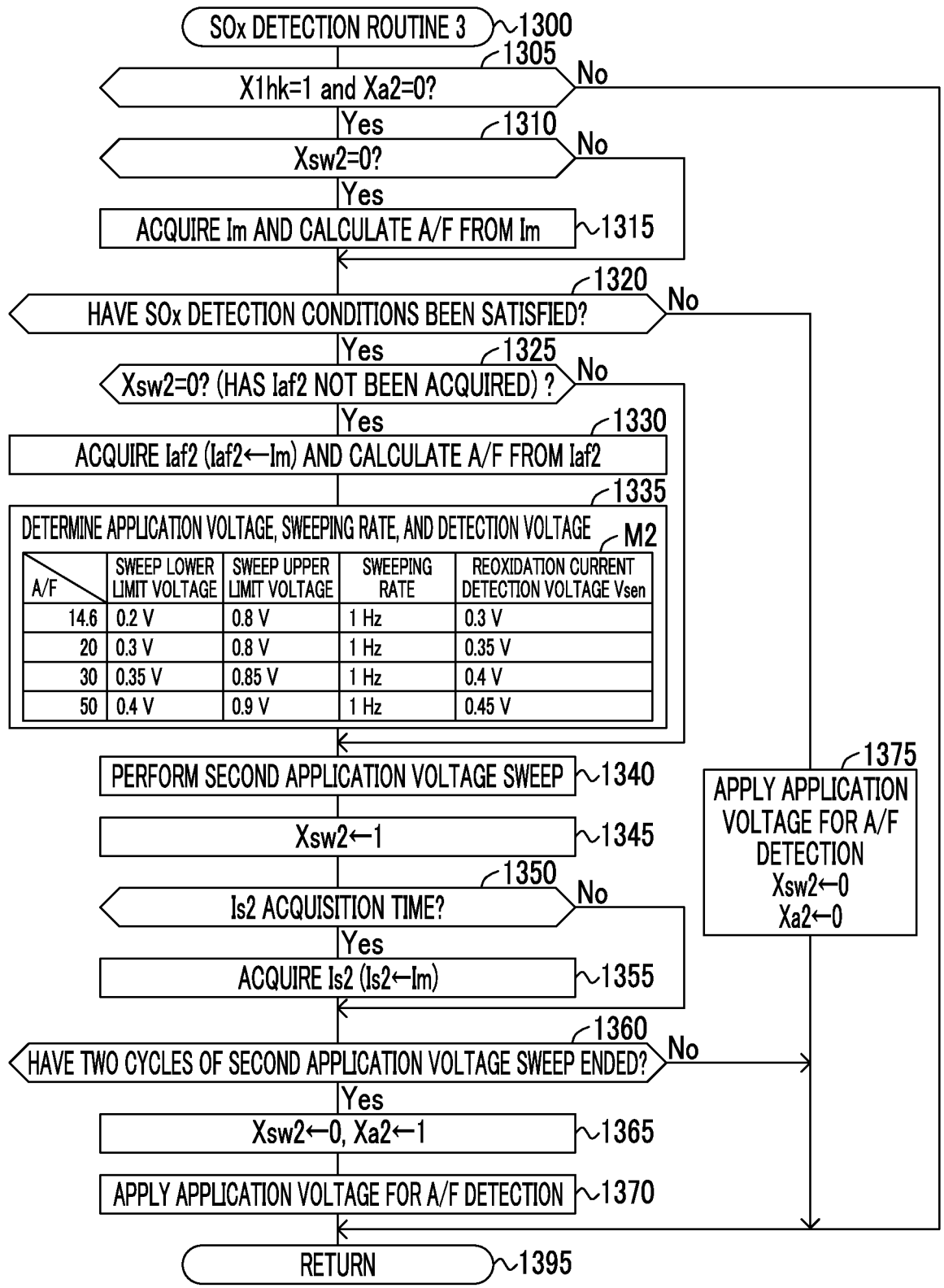
FIG. 13 is a flowchart illustrating SOx detection routine 3 which is performed by the CPU of the ECU illustrated in FIG. 1.

By performing the routine illustrated in FIG. 13, the third current Iaf2 and the fourth current Is2 are acquired and stored in the RAM.

SOx detection routine 4 will be described below with reference to FIG. 14. The CPU starts this routine from Step 1400 in FIG. 14 at a predetermined time and determines whether the value of the second acquisition completion flag Xa2 is "1" in Step 1405.

SOx detection routine 4 functions substantially when the value of the second acquisition completion flag Xa2 is "1." Accordingly, when the value of the second acquisition completion flag Xa2 is not "1," the CPU determines "NO" in Step 1405 and temporarily ends this routine in Step 1495.

On the other hand, when the value of the second acquisition completion flag Xa2 is set to "1" through the process of Step 1365 in FIG. 13, the CPU determines "YES" in Step 1405 and determines whether the air-fuel ratio A/F of the engine (the oxygen concentration in the exhaust gas) when the first application voltage sweep is performed and the air-fuel ratio A/F of the engine (the oxygen concentration in the exhaust gas) when the second application voltage sweep is performed are within a predetermined range based on an absolute value of a difference (Iv (=|Iaf1−Iaf2|) between the first current Iaf1 and the third current Iaf2 in Step 1410. That is, the CPU determines whether the absolute value of the difference Iv is equal to or less than a predetermined value Ivth.

When the absolute value of the difference Iv is equal to or less than the predetermined value Ivth, the CPU determines "YES" in Step 1410 and calculates the parameters Ia1 (=Iaf1−Is1) and Ia2 (=Iaf2−Is2) and the SOx detection parameter (the difference Id (=Ia2−Ia1)) using the "first current Iaf1, the second current Is1, the third current Iaf2, and the fourth current Is2" which have been already acquired in Step 1415.

Thereafter, in Step 1420, the CPU determines whether the SOx detection parameter Id is equal to or greater than a threshold difference Idth.

When the difference Id is equal to or greater than the threshold difference Idth, the CPU determines "YES" in Step 1420 and determines that SOx with a predetermined concentration (a concentration corresponding to the threshold difference Idth) or higher is contained in the exhaust gas in Step 1425. At this time, the CPU may store the purport indicating that SOx with a predetermined concentration or higher is contained in the exhaust gas (or the purport indicating that S exceeding an allowable value is mixed into fuel) in the backup RAM or may turn on a predetermined warning lamp. Thereafter, in Step 1430, the CPU sets the value of the SOx detection completion flag XSOx to "1." Thereafter, the CPU temporarily ends this routine in Step 1495.

On the other hand, when the SOx detection parameter Id is not equal to or greater than the threshold difference Idth (that is, less than the threshold difference Idth), the CPU determines "NO" in Step 1420 and determines that SOx with a predetermined concentration or higher is not contained in the exhaust gas in Step 1435. At this time, the CPU may store the purport indicating that SOx with a predetermined concentration or higher is not contained in the exhaust gas (or the purport indicating that S exceeding an allowable value is not mixed into fuel) in the backup RAM or may turn on a predetermined warning lamp. Thereafter, in Step 1430, the CPU sets the value of the SOx detection completion flag XSOx to "1." Thereafter, the CPU temporarily ends this routine in Step 1495.

When the absolute value of the difference Iv is greater than the predetermined value Ivth at a time point at which the process of Step 1410 is performed, the CPU determines "NO" in Step 1410 and performs Step 1440.

As described above, the first parameter Ia1 is calculated by subtracting the second current Is1 from the first current Iaf1 (first parameter Ia1=first current Iaf1−second current Is1). The first current Iaf1 corresponds to the oxygen concentration during the first application voltage sweep when the second current Is1 is acquired. Accordingly, an influence of the oxygen concentration is removed from the first parameter Ia1. Similarly, the second parameter Ia2 is calculated by subtracting the fourth current Is2 from the third current Iaf2 (second parameter Ia2=third current Iaf2−fourth current Is2). The third current Iaf2 corresponds to the oxygen concentration during the second application voltage sweep when the fourth current Is2 is acquired. Accordingly, an influence of the oxygen concentration is removed from the second parameter Ia2.

However, when the absolute value of the difference Iv is greater than the predetermined value Ivth, that is, when the magnitude of the difference between the oxygen concentration during the first application voltage sweep and the oxygen concentration during the second application voltage sweep is large, an influence of the difference in oxygen concentration cannot be completely removed from the "first parameter Ia1 and the second parameter Ia2" and thus a likelihood that the SOx detection parameter (the difference Id) will accurately indicate only the output current change due to the SOx reaction decreases. In some embodiments, when the absolute value of the difference Iv is greater than the predetermined value Ivth, the SOx concentration may not be detected using the SOx detection parameter (the difference Id) acquired in Step 1415.

Therefore, in this case, the CPU transitions the routine from Step 1410 to Step 1440 and prevents the SOx concentration detection using the SOx detection parameter (the difference Id) from being performed by setting (clearing) the values of the following flags, which have been set to "1," to "0."

First acquisition completion flag Xa1
Second acquisition completion flag Xa2
First voltage maintaining process completion flag X1$hk$ Thereafter, the CPU temporarily ends this routine in Step 1495. In this case, since the value of the sensor activation flag Xact is "1" and the value of the first acquisition completion flag Xa1 is "0," the CPU determines "YES" in Step 1105 of SOx detection routine 1. Accordingly, SOx detection routine 1 functions substantially again.

As described above, the first detection device calculates the difference Id between the second parameter Ia2 and the first parameter Ia1 as the SOx detection parameter Id and performs the SOx concentration detection using the calculated SOx detection parameter Id. The SOx detection parameter Id (the difference (Id) has a value substantially based on only the concentration of sulfur oxide in the exhaust gas and has a value from which an influence of components varying depending on individual differences between the gas sensors 30 is reduced. Accordingly, the first detection device can accurately determine whether SOx with a predetermined concentration or higher is contained in the exhaust gas.

Second Embodiment

A gas detection device according to a second embodiment of the disclosure (hereinafter also referred to as a "second detection device") will be described below. The second detection device is different from the first detection device, only in that a "ratio Ir (=Ia2/Ia1)" instead of the "difference Id (=Ia2−Ia1)" is used as the SOx detection parameter which is used for SOx concentration detection.

As described above, the first parameter Ia1 is not or hardly affected by any of the influence of the concentration of oxygen in the exhaust gas and the influence of the concentration of sulfur oxides in the exhaust gas and has a value in which the influence of individual differences between the gas sensors 30 is reflected. On the other hand, the second parameter Ia2 is not or hardly affected by the influence of the oxygen concentration in the exhaust gas and has a value which varies depending on the SOx concentration and in which the influence of individual differences between the gas sensors 30 is reflected. Accordingly, the ratio Ir (=Ia2/Ia1) of the second parameter Ia2 to the first parameter Ia1 has a value based on only the concentration SOx in the exhaust gas and can be said to have a value from which the influence of individual differences between the gas sensors 30 is greatly removed, but not completely removed. This difference will be mainly described below.

Specific Operation

A specific operation of the second detection device will be described below. The CPU of the ECU 20 performs the routines illustrated in FIGS. 10 to 13 and a routine illustrated in FIG. 15 instead of FIG. 14 at predetermined time intervals. The operation based on the routines illustrated in FIGS. 10 to 13 is the same as the operation based on the routines in the first detection device and has been described above. Therefore, description thereof will not be repeated.

The operation of the second detection device will be described below with reference to FIG. 15. The routine illustrated in FIG. 15 is different from the routine illustrated in FIG. 14, only in that Steps 1415 and 1420 in FIG. 14 are replaced with Steps 1515 and 1520. This difference will be mainly described below.

When Step 1410 transitions to Step 1515, the CPU calculates the parameters Ia1 (=Iaf1−Is1) and Ia2 (=Iaf2−Is2) and the ratio Ir (=Ia2/Ia1) using the first current Iaf1, the second current Ias1, the third current Iaf2, and the fourth current Is2 and then performs Step 1520.

In Step 1520, the CPU determines whether the ratio Ir is equal to or greater than a threshold ratio Irth. When the ratio Ir is equal to or greater than the threshold ratio Irth, the CPU determines "YES" in Step 1520 and determines that SOx with a predetermined concentration (a concentration corresponding to the threshold ratio Irth) or higher is contained in the exhaust gas in Step 1425. At this time, the CPU may store the purport indicating that SOx with a predetermined concentration or higher is contained in the exhaust gas (or the purport indicating that S exceeding an allowable value is mixed into fuel) in the backup RAM or may turn on a predetermined warning lamp. Thereafter, the CPU performs Step 1430.

On the other hand, when the ratio Ir is not equal to or greater than the threshold ratio Irth (that is, less than the threshold ratio Irth), the CPU determines "NO" in Step 1520 and determines that SOx with a predetermined concentration or higher is not contained in the exhaust gas in Step 1435. At this time, the CPU may store the purport indicating that SOx with a predetermined concentration or higher is not contained in the exhaust gas (or the purport indicating that S exceeding an allowable value is not mixed into fuel) in the backup RAM or may turn on a predetermined warning lamp. Thereafter, the CPU performs Step 1430.

As described above, the ECU of the second detection device calculates the ratio Ir (=Ia2/Ia1) of the second parameter Ia2 to the first parameter Ia1 as the SOx detection parameter Ir and performs the SOx concentration detection using the calculated SOx detection parameter Ir. The SOx detection parameter Ir has a value substantially based on only the concentration of sulfur oxide in the exhaust gas and has a value from which an influence of components varying depending on individual differences between the gas sensors 30 is reduced. Accordingly, the second detection device can accurately determine whether SOx with a predetermined concentration or higher is contained in the exhaust gas.

MODIFIED EXAMPLES

While embodiments of the disclosure have been described above specifically, the disclosure is not limited to the embodiments but can employ various modified examples based on the technical concept of the disclosure.

In the above-mentioned embodiments, without being limited to the "output current Im when the application voltage Vm becomes the reoxidation current detection voltage Vsen which is a voltage lower than the decomposition start voltage of SOx," but any value having a correlation with the output current Im in a period in which the application voltage Vm is lower than the decomposition start voltage of SOx during the step-down sweep may be acquired as the second current Is1 or the fourth current Is2. For example, in the embodiments, a minimum value of the output current Im in a period in which the application voltage Vm is within a detection voltage range during the step-down sweep may be acquired as the second current Is1 or the fourth current Is2. In this case, the detection voltage range is a range which is equal to or higher than a predetermined voltage higher than the lower limit voltage (the first voltage V1) of the step-down sweep and which is equal to or lower than the decomposition start voltage of SOx (0.6 V).

Modified Example of First Detection Device

The first detection device determines whether SOx with a predetermined concentration or higher is contained in the exhaust gas by comparing the magnitude of the difference Id with the threshold difference Idth, but the concentration of SOx in the exhaust gas may be acquired based on the difference Id as will be described below.

Figure 14:
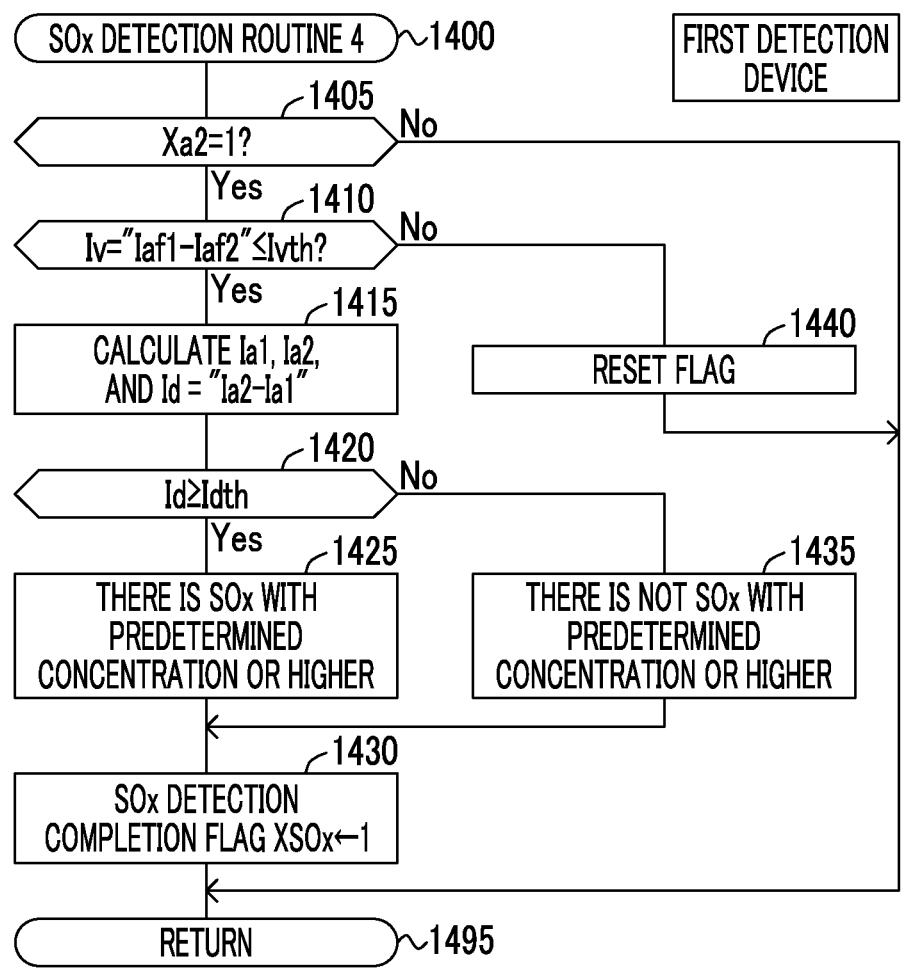
FIG. 14 is a flowchart illustrating SOx detection routine 4 which is performed by the CPU of the ECU illustrated in FIG. 1.
Figure 15:
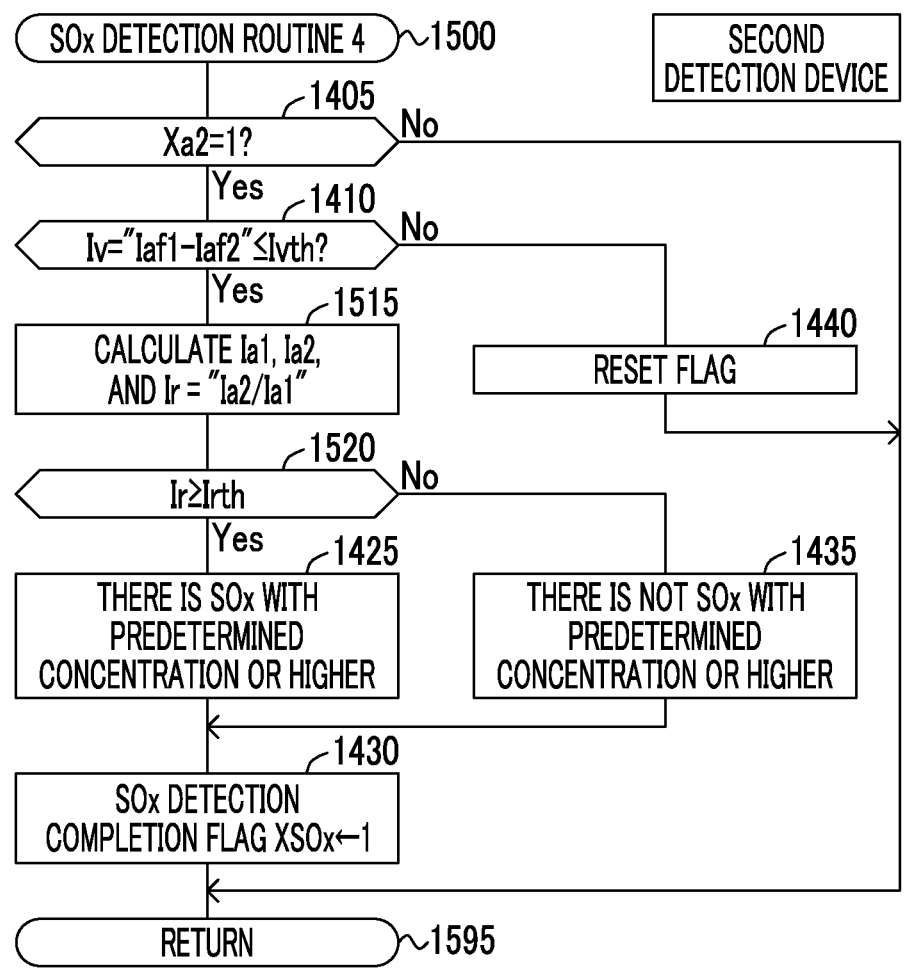
FIG. 15 is a flowchart illustrating SOx detection routine 5 which is performed by a CPU of an ECU in a gas detection device according to a second embodiment of the disclosure.
Figure 16:
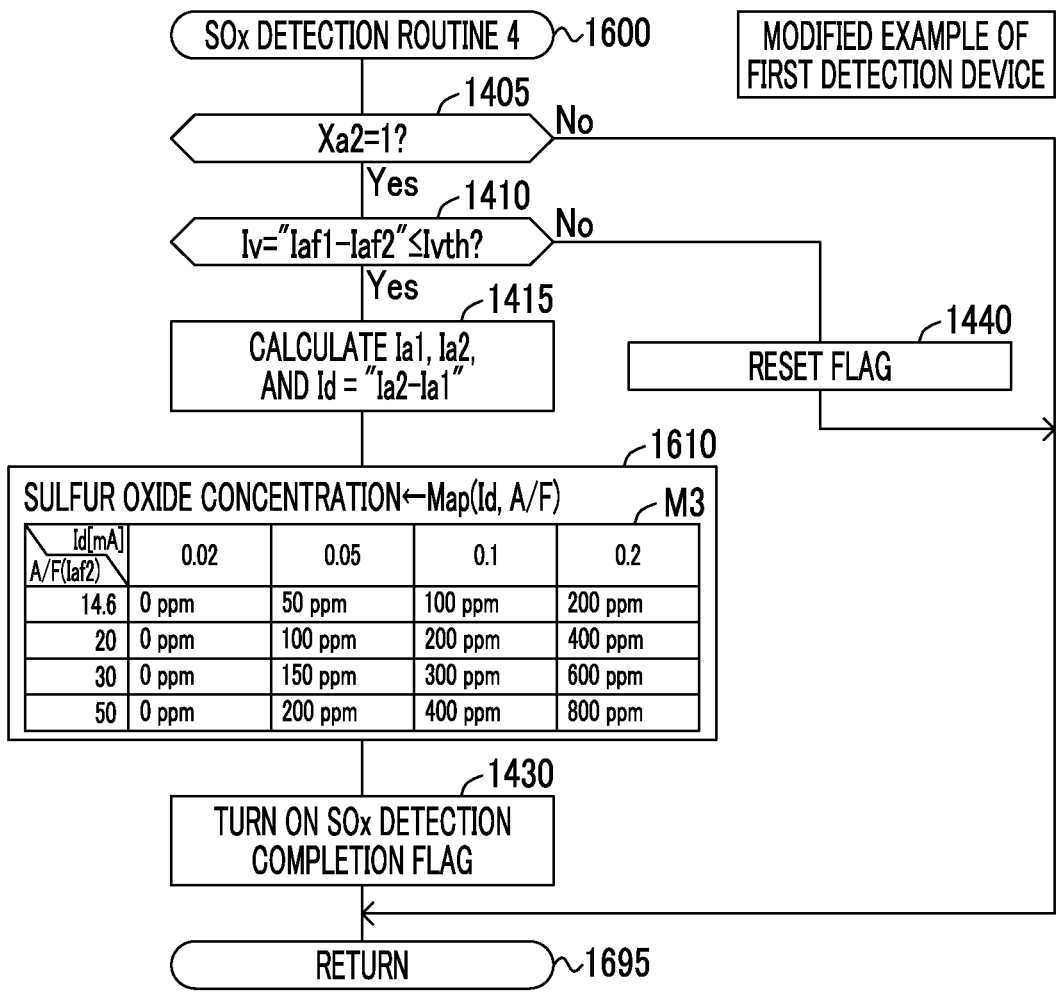
FIG. 16 is a flowchart illustrating SOx detection routine 4 which is performed by the CPU of the ECU according to a modified example of the gas detection device illustrated in FIG. 1.

For example, the CPU may be configured to perform SOx detection routine 4 illustrated in FIG. 16 instead of SOx detection routine 4 illustrated in FIG. 14. The routine illustrated in FIG. 16 is a routine in which the "process of Step 1610" is performed instead of the processes of "Steps 1420, 1425, and 1435" in the routine illustrated in FIG. 14. Accordingly, the process of "Step 1610" in FIG. 16 will be mainly described below.

When the difference Id is calculated in Step 1415 of FIG. 16, the CPU acquires the concentration of SOx in the exhaust gas by applying the difference Id and the A/F (or Iaf2) calculated based on Iaf2 acquired in Step 1330 in FIG. 13 to a lookup table Map1 (Id, A/F) in Step 1610. The ROM (the storage unit) of the ECU 20 stores a "relationship between the difference Id and A/F and the concentration of SOx in the exhaust gas" as a lookup table Map1 (Id, A/F) (see block M3 in FIG. 16). The lookup table can be acquired by performing an experiment or the like in advance.

Modified Example of Second Detection Device

The second detection device determines whether SOx with a predetermined concentration or higher is contained in the exhaust gas by comparing the magnitude of the ratio Ir with the threshold ratio Irth, but the concentration of SOx in the exhaust gas may be acquired based on the ratio Ir as will be described below.

Figure 17:
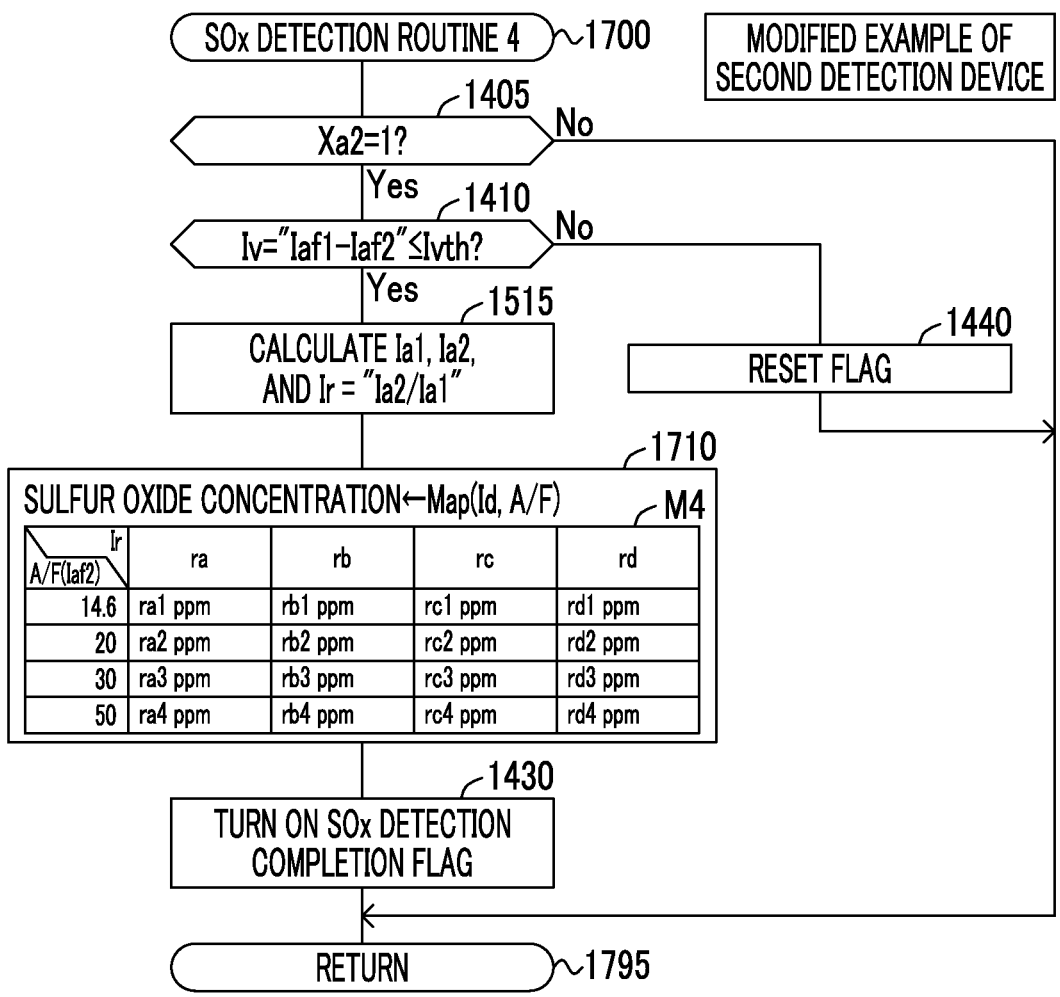
FIG. 17 is a flowchart illustrating a SOx detection routine which is performed by the CPU of the ECU according to another modified example of the gas detection device illustrated in FIG. 1.

For example, the CPU may be configured to perform SOx detection routine 4 illustrated in FIG. 17 instead of SOx detection routine 4 illustrated in FIG. 15. The routine illustrated in FIG. 17 is a routine in which the "process of Step 1710" is performed instead of the processes of "Steps 1520, 1425, and 1435" in the routine illustrated in FIG. 15. Accordingly, the process of "Step 1710" in FIG. 17 will be mainly described below.

When the ratio Ir is calculated in Step 1515 of FIG. 17, the CPU acquires the concentration of SOx in the exhaust gas by applying the ratio Ir and the A/F (or Iaf2) calculated based on Iaf2 acquired in Step 1330 in FIG. 13 to a lookup table Map2 (Ir, A/F) in Step 1710. The ROM (the storage unit) of the ECU 20 stores a "relationship between the ratio Ir and A/F and the concentration of SOx in the exhaust gas" as a lookup table Map2 (Ir, A/F) (see block M4 in FIG. 17). The lookup table can be acquired by performing an experiment or the like in advance.

The ECU 20 in each modified example is configured to acquire the concentration of SOx in the exhaust gas corresponding to the difference Id or the ratio Ir from the lookup table stored in the ROM using the difference Id or the ratio Ir as the SOx detection parameter which is not easily affected by the individual characteristics of the gas sensor, is not affected by oxygen-containing components other than SOx contained in the exhaust gas, and represents the reoxidation current change. Accordingly, it is possible to accurately detect a concentration of sulfur oxide in an exhaust gas.

For example, the voltage waveform of the application voltage sweep is not limited the waveforms illustrated in FIGS. 7B and 7C, but may be an arbitrary waveform (for example, a triangular waveform) as long as the step-down sweep is performed with a voltage varying continuously and at a step-down rate at which the reoxidation current change due to a reoxidation reaction of sulfur adsorbed on the first electrode 41a becomes very remarkable from a time point of the step-down sweep of the second application voltage sweep. In this case, the waveform of the first application voltage sweep has to be set to the same as the waveform of the second application voltage sweep, except for the application voltage range.

What is claimed is:

1. A gas detection device comprising:
   an element portion which is disposed in an exhaust gas passage of an internal combustion engine, which includes an electrochemical cell including a solid electrolyte with oxide ion conductivity and a first electrode and a second electrode which are formed on surfaces of the solid electrolyte, and a diffusion resistor formed of a porous material being able to transmit an exhaust gas flowing in the exhaust gas passage, and in which the exhaust gas flowing in the exhaust gas passage reaches the first electrode via the diffusion resistor;
   a voltage applying unit configured to apply a voltage across the first electrode and the second electrode;
   a current detecting unit configured to detect an output current which is a current flowing between the first electrode and the second electrode; and
   an electronic control unit configured to control an application voltage which is a voltage applied across the first electrode and the second electrode using the voltage applying unit, to acquire the output current using the current detecting unit, and to perform determination of whether sulfur oxides with a predetermined concentration or higher are contained in the exhaust gas or detection of a concentration of sulfur oxides in the exhaust gas based on the acquired output current,
   wherein the electronic control unit is configured to perform a first application voltage sweep of performing a first step-up sweep of stepping up the application voltage from a first voltage which is selected in a first voltage range higher than a lower limit voltage of a limiting current region in which the output current is a limiting current of oxygen and lower than a decomposition start voltage of sulfur oxides to a second voltage which is higher than the first voltage and equal to or lower than a voltage higher by a predetermined value than the decomposition start voltage of sulfur oxides and then performing a first step-down sweep of stepping down the application voltage from the second voltage to the first voltage in at least one cycle and to acquire a first parameter using at least the output current in the first step-down sweep and using a predetermined first specific method,
   the electronic control unit is configured to perform a second application voltage sweep of performing a second step-up sweep of stepping up the application voltage from a third voltage which is selected in the first voltage range to a fourth voltage which is higher than the decomposition start voltage of sulfur oxides and higher than the second voltage and then performing a second step-down sweep of stepping down the application voltage from the fourth voltage to the third voltage using the voltage applying unit in at least one cycle after the first application voltage sweep is performed and to acquire a second parameter having a correlation with a degree of change occurring in the output current, which increases as the concentration of sulfur oxides contained in the exhaust gas increases, due to a current flowing between the first electrode and the second electrode due to return of sulfur adsorbed on the first electrode to sulfur oxides by a reoxidation reaction in the first electrode when the application voltage is lower than the decomposition start voltage of sulfur oxides in a period in which the second step-down sweep is performed using at least the output current in the second step-down sweep and using the same second specific method as the first specific method, and
   the electronic control unit is configured to calculate a difference or a ratio between the first parameter and the second parameter as a SOx detection parameter and to perform determination of whether sulfur oxides with a predetermined concentration or higher are contained in the exhaust gas or detection of the concentration of sulfur oxides in the exhaust gas based on the SOx detection parameter.

2. The gas detection device according to claim 1, wherein a step-down rate of the second step-down sweep is set to a rate at which a rate of the reoxidation reaction increases rapidly at a time point at which the application voltage reaches a voltage in a voltage range which is within the first voltage range and higher than the third voltage, and
   the first application voltage sweep and the second application voltage sweep have the same sweeping rate which is expressed by a voltage change per unit time.

3. The gas detection device according to claim 1, wherein the electronic control unit is configured to use a method of setting the application voltage to an air-fuel ratio detection application voltage in the limiting current region using the voltage applying unit before the first application voltage sweep is performed, acquiring the output current detected by the current detecting unit as a first current when the application voltage is set to the air-fuel ratio detection application voltage, acquiring a value having a specific correlation with the output current in a predetermined first period in the first step-down sweep as a second current based on the output current detected by the current detecting unit, and calculating a difference between the acquired first current and the acquired second current as the first specific method to acquire the calculated difference as the first parameter, and the electronic control unit is configured to use a method of setting the application voltage to the air-fuel ratio detection application voltage using the voltage applying unit after the first application voltage sweep is performed and before the second application voltage sweep is performed, acquiring the output current detected by the current detecting unit when the application voltage is set to the air-fuel ratio detection application voltage as a third current, acquiring a value having the specific correlation with the output current in a second period in which the application voltage is in a range which is higher than the third voltage and equal to or lower than the decomposition start voltage of sulfur oxides in the second step-down sweep as a fourth current based on the output current detected by the current detecting unit, and calculating a difference between the acquired third current and the acquired fourth current as the second specific method to acquire the calculated difference as the second parameter.

4. The gas detection device according to claim 3, wherein the electronic control unit is configured to acquire the output current detected by the current detecting unit when the application voltage is a predetermined current detection voltage in a range which is higher than the first voltage and equal to or lower than the decomposition start voltage of sulfur oxides in the first step-down sweep as the second current which has a value having the specific correlation with the output current in the first period, and the electronic control unit is configured to acquire the output current detected by the current detecting unit when the application voltage is the current detection voltage in the second step-down sweep as the fourth current which has a value having the specific correlation with the output current in the second period.

5. The gas detection device according to claim 3, wherein the electronic control unit is configured to determine whether a magnitude of a difference between the first current and the third current is equal to or less than a threshold difference value, and the electronic control unit is configured to perform the determination of whether sulfur oxides with a predetermined concentration or higher are contained in the exhaust gas or the detection of the concentration of sulfur oxides in the exhaust gas only when the magnitude of the difference is equal to or less than the threshold difference value.

6. The gas detection device according to claim 3, wherein the electronic control unit is configured to detect the concentration of sulfur oxides based on the SOx detection parameter and the third current.

7. The gas detection device according to claim 1, wherein the electronic control unit is configured to determine whether a magnitude of the SOx detection parameter is equal to or greater than a predetermined threshold value, and the electronic control unit is configured to determine that sulfur oxides with a predetermined concentration or higher are contained in the exhaust gas when it is determined that the magnitude of the SOx detection parameter is equal to or greater than the threshold value, and to determine that sulfur oxides with a predetermined concentration or higher are not contained in the exhaust gas when it is determined that the magnitude of the SOx detection parameter is less than the threshold value.

* * * * *

UNITED STATES PATENT AND TRADEMARK OFFICE
CERTIFICATE OF CORRECTION

PATENT NO. : 10,605,765 B2  
APPLICATION NO. : 15/841924  
DATED : March 31, 2020  
INVENTOR(S) : Keiichiro Aoki, Kazuhiro Wakao and Kazuhisa Matsuda Page 1 of 1

It is certified that error appears in the above-identified patent and that said Letters Patent is hereby corrected as shown below:

On the Title Page

Item (72), inventor 1, city, delete "Shizuoka-ken" and insert --Sunto-gun Shizuoka-ken--, therefor.

Item (72), inventor 2, city, delete "Susono" and insert --Susono-shi Shizuoka-ken--, therefor.

Item (72), inventor 3, city, delete "Susono" and insert --Susono-shi Shizuoka-ken--, therefor.

In the Specification

In Column 1, Line 57, delete ""current" and insert --current--, therefor.

Signed and Sealed this  
Twenty-sixth Day of May, 2020

Andrei Iancu  
*Director of the United States Patent and Trademark Office*